(12) United States Patent
McKenzie et al.

(10) Patent No.: US 9,364,534 B2
(45) Date of Patent: *Jun. 14, 2016

(54) TREATMENT OF NEUROLOGICAL CONDITIONS

(75) Inventors: Brent Steven McKenzie, Hoppers Crossing (AU); Peter Frederick Curwen, Kensington (AU); Eugene Maraskovsky, Kew (AU)

(73) Assignee: CSL LIMITED, Parkville (AU)

(*) Notice: Subject to any disclaimer, the term of this patent is extended or adjusted under 35 U.S.C. 154(b) by 644 days.

This patent is subject to a terminal disclaimer.

(21) Appl. No.: 12/881,293

(22) Filed: Sep. 14, 2010

(65) Prior Publication Data

US 2011/0091456 A1 Apr. 21, 2011

Related U.S. Application Data

(60) Provisional application No. 61/242,503, filed on Sep. 15, 2009.

(51) Int. Cl.
| A61K 39/395 | (2006.01) |
| A61K 31/7088 | (2006.01) |
| C07K 16/24 | (2006.01) |
| C07K 16/28 | (2006.01) |
| A61K 45/06 | (2006.01) |
| C12N 15/113 | (2010.01) |
| A61K 39/00 | (2006.01) |

(52) U.S. Cl.
CPC ......... *A61K 39/3955* (2013.01); *A61K 31/7088* (2013.01); *A61K 45/06* (2013.01); *C07K 16/243* (2013.01); *C07K 16/2866* (2013.01); *C12N 15/1136* (2013.01); *C12N 15/1138* (2013.01); *A61K 2039/505* (2013.01); *C07K 2317/73* (2013.01)

(58) Field of Classification Search
None
See application file for complete search history.

(56) References Cited

U.S. PATENT DOCUMENTS

| 7,108,852 B2* | 9/2006 | Devalaraja et al. ........ 424/130.1 |
| 7,618,632 B2* | 11/2009 | Collins et al. .............. 424/144.1 |
| 2007/0071675 A1 | 3/2007 | Wu et al. |

FOREIGN PATENT DOCUMENTS

| WO | 2005/121174 A2 | 12/2005 |
| WO | 2008/003763 A1 | 1/2008 |
| WO | 2008/017126 A1 | 2/2008 |
| WO | 2008/125903 A2 | 10/2008 |

OTHER PUBLICATIONS

McQualter et al. Granulocyte macrophage colony-stimulating factor: a new putative therapeutic target in multiple sclerosis. J Exp Med. Oct. 1, 2001;194(7):873-82.*

Openshaw et al. Multiple sclerosis flares associated with recombinant granulocyte colony-stimulating factor. Neurology. Jun. 13, 2000;54(11):2147-50.*

Brendolan, A. et al., "Treatment of adjuvant arthritis with granulocyte-colony stimulating factor and peptide derived from heat shock protein 65", Cellular Immunology, 221:6-14 (2003).

Franzke, A., et al., "G-CSF as immune regulator in T cells expressing the G-CSF receptor: implications for transplantation and autoimmune diseases", Blood, 102(2):734-739 (2002).

Lieschke, GJ., et al., "Mice Lacking Grannlocyte Colony-Stimulating Factor Have Chronic Neutropenia, Granulocyte and Macrophage Progenitor Cell Deficiency, and Impaired Neutrophil Mobilization", Blood, 84(6):1737-1746 (1994).

Lock, C., et al., "Gene-microarray analysis of multiple sclerosis lesions yields new targets validated in autoimmune encephalomyelitis", Nature Medicine, 8(5):500-508 (2002).

Stanley, E., et al., "Granulocyte/macrophage colony-stimulating factor-deficient mice show no major perturbation of hematopoiesis but develop a characteristic pulmonary pathology", Proc. Natl. Acad. Sci., 91:5592-5596 (1994).

Yong, K. L., Granulocyte colony-stimulating factor (G-CSF) increases neutrophil migration across vascular endothelium independent of an effect on adhesion: comparison with granulocyte-macrophage colony-stimulating factor (GM-CSF), British Journal of Haematology, 94:40-47(1996).

Zavala, F., et al., "G-CSF Therapy of Ongoing Experimental Allergic Encephalomyelitis Via Chemokine- and Cytokine-Based Immune Deviation", The Journal of Immunology, 168:2011-2019 (2002).

Cornish, A. L et al., "G-CSF and CM-CSF as therapeutic targets in rheumatoid arthritis" Nature Reviews Rheumatology (2009) pp. 554-559, vol. 5, No. 10.

Snir, O. et al., "G-CSF enhances the adhesion of encephalitogenic T cells to extracellular matrix components: A possible mechanism for exacerbation of multiple sclerosis" Journal of Neuroimmunology (2006) pp. 145-155, vol. 172.

Supplementary European Search Report dated Jun. 4, 2013 issued in European Application No. 10816462.5-1456 / 2477656 PCT/AU2010001191.

International Search Report dated Nov. 17, 2010 issued in International Application No. PCT/AU2010/001191.

Ward, A.C. et al., "Novel Point Mutation in the Extracellular Domain of the Granulocyte Colony-stimulating Factor (G-CSF) Receptor in a Case of Severe Congenital Neutropenia Hyporesponsive to G-CSF Treatment" J. Exp. Med (Aug. 16, 1999) pp. 497-507, vol. 190, No. 4.

(Continued)

*Primary Examiner* — Gregory S Emch
(74) *Attorney, Agent, or Firm* — Scully Scott Murphy & Presser

(57) ABSTRACT

The present invention is directed to a method for treating an inflammatory neurodegenerative condition of the CNS in a subject comprising administering to said subject a G-CSF or G-CSFR inhibiting agent selected from the group consisting of an antibody specific for G-CSF or G-CSFR, a soluble G-CSFR or a G-CSF-binding portion thereof and a 20 to 30 nucleotide sense or antisense molecule targeted to a nucleic acid molecule encoding G-CSF.

7 Claims, 4 Drawing Sheets

(56) References Cited

OTHER PUBLICATIONS

Dong, F. et al., "Identification of a nonsense mutation in the granulocyte-colony-stimulating factor receptor in severe congenital neutropenia" Proc. Natl. Acad. Sci. USA (May 10, 1994) pp. 4480-4484, vol. 91, No. 10.

Druhan, L.J. et al., "Novel mechanism of G-SF refractoriness in patients with severe congenital neutropenia" Blood (Jan. 15, 2005) pp. 584-591, vol. 105, No. 2.

Hammond, W.P. et al., "Chronic Neutropenia: A new model induced by Human Granulocyte Colony-stimulating Factor" The Journal of Clinical Investigation (Feb. 1991) pp. 704-710, vol. 87, No. 2.

Burt, R.K. et al., "Treatment of Autoimmune Disease by Intense Immunosuppressive Conditioning and Autologous Hematopoietic Stem Cell Transplantation" Blood (Nov. 15, 1998) pp. 3505-3514, vol. 92, No. 10.

Renwick, W. et al., "Use of Filgrastim and Pegfilgratim to Support Delivery of Chemotherapy: twenty years of clinical experience" Biodrugs (2009) pp. 175-186, vol. 23, No. 3.

Hellmich, B. et al., "Autoantibodies Against Granulocyte Colony-Stimulating Factor in Felty's Syndrome and Neutropenic Systemic Lupus Erythematosus" Arthritis & Rheumatism (Sep. 2002) pp. 2384-2391, vol. 46, No. 9.

Lund, B.T. et al., "Increased CXCL8 (IL-8) expression in Multiple Sclerosis" Journal of Neuroimmunology (Oct. 2004) pp. 161-171, vol. 155, No. 1-2.

\* cited by examiner

SEQUENCE LISTING

```
<160> NUMBER OF SEQ ID NOS: 8

<210> SEQ ID NO 1
<211> LENGTH: 204
<212> TYPE: PRT
<213> ORGANISM: homo sapiens
```

<400> SEQUENCE: 1

| | | | | | | | | | | | | | | |
|---|---|---|---|---|---|---|---|---|---|---|---|---|---|---|
| Met | Ala | Gly | Pro | Ala | Thr | Gln | Ser | Pro | Met | Lys | Leu | Met | Ala | Leu | Gln |
| 1 | | | | 5 | | | | | 10 | | | | | 15 | |
| Leu | Leu | Leu | Trp | His | Ser | Ala | Leu | Trp | Thr | Val | Gln | Glu | Ala | Thr | Pro |
| | | | 20 | | | | | 25 | | | | | 30 | | |
| Leu | Gly | Pro | Ala | Ser | Ser | Leu | Pro | Gln | Ser | Phe | Leu | Leu | Lys | Cys | Leu |
| | | 35 | | | | | 40 | | | | | 45 | | | |
| Glu | Gln | Val | Arg | Lys | Ile | Gln | Gly | Asp | Gly | Ala | Ala | Leu | Gln | Glu | Lys |
| | 50 | | | | | 55 | | | | | 60 | | | | |
| Leu | Cys | Ala | Thr | Tyr | Lys | Leu | Cys | His | Pro | Glu | Glu | Leu | Val | Leu | Leu |
| 65 | | | | | 70 | | | | | 75 | | | | | 80 |
| Gly | His | Ser | Leu | Gly | Ile | Pro | Trp | Ala | Pro | Leu | Ser | Ser | Cys | Pro | Ser |
| | | | | 85 | | | | | 90 | | | | | 95 | |
| Gln | Ala | Leu | Gln | Leu | Ala | Gly | Cys | Leu | Ser | Gln | Leu | His | Ser | Gly | Leu |
| | | | 100 | | | | | 105 | | | | | 110 | | |
| Phe | Leu | Tyr | Gln | Gly | Leu | Leu | Gln | Ala | Leu | Glu | Gly | Ile | Ser | Pro | Glu |
| | | 115 | | | | | 120 | | | | | 125 | | | |
| Leu | Gly | Pro | Thr | Leu | Asp | Thr | Leu | Gln | Leu | Asp | Val | Ala | Asp | Phe | Ala |
| | 130 | | | | | 135 | | | | | 140 | | | | |
| Thr | Thr | Ile | Trp | Gln | Gln | Met | Glu | Glu | Leu | Gly | Met | Ala | Pro | Ala | Leu |
| 145 | | | | | 150 | | | | | 155 | | | | | 160 |
| Gln | Pro | Thr | Gln | Gly | Ala | Met | Pro | Ala | Phe | Ala | Ser | Ala | Phe | Gln | Arg |
| | | | | 165 | | | | | 170 | | | | | 175 | |
| Arg | Ala | Gly | Gly | Val | Leu | Val | Ala | Ser | His | Leu | Gln | Ser | Phe | Leu | Glu |
| | | | 180 | | | | | 185 | | | | | 190 | | |
| Val | Ser | Tyr | Arg | Val | Leu | Arg | His | Leu | Ala | Gln | Pro | | | | |
| | | 195 | | | | | 200 | | | | | | | | |

<210> SEQ ID NO 2
<211> LENGTH: 1498
<212> TYPE: DNA
<213> ORGANISM: homo sapiens

<400> SEQUENCE: 2

```
ggagcctgca gcccagcccc acccagaccc atggctggac ctgccaccca gagccccatg      60
aagctgatgg ccctgcagct gctgctgtgg cacagtgcac tctggacagt gcaggaagcc     120
acccccctgg gccctgccag ctccctgccc cagagcttcc tgctcaagtg cttagagcaa     180
gtgaggaaga tccagggcga tggcgcagcg ctccaggaga agctgtgtgc cacctacaag     240
ctgtgccacc ccgaggagct ggtgctgctc ggacactctc tgggcatccc ctgggctccc     300
ctgagcagct gccccagcca ggccctgcag ctggcaggct gcttgagcca actccatagc     360
ggccttttcc tctaccaggg gctcctgcag gccctggaag gatctccccc cgagttgggt     420
cccaccttgg acacactgca gctggacgtc gccgactttg ccaccaccat ctggcagcag     480
atggaagaac tgggaatggc ccctgccctg cagcccaccc aggtgccat gccggccttc     540 gcctctgctt tccagcgccg gcaggaggg gtcctagttg cctcccatct gcagagcttc     600
ctggaggtgt cgtaccgcgt tctacgccac cttgcccagc cctgagccaa gccctcccca     660
tcccatgtat ttatctctat ttaatattta tgtctattta agcctcatat ttaaagacag     720
ggaagagcag aacggagccc caggcctctg tgtccttccc tgcatttctg agtttcattc     780
tcctgcctgt agcagtgaga aaaagctcct gtcctcccat ccctggact gggaggtaga     840 taggtaaata ccaagtattt attactatga ctgctcccca gccctggctc tgcaatgggc     900
```

```
actgggatga gccgctgtga gccctggtc ctgagggtcc ccacctggga ccccttgagag    960 tatcaggtct cccacgtggg agacaagaaa tccctgttta atatttaaac agcagtgttc   1020
cccatctggg tccttgcacc cctcactctg gcctcagccg actgcacagc ggcccctgca   1080
tccccttggc tgtgaggccc ctggacaagc agaggtggcc agagctggga ggcatggccc   1140
tggggtccca cgaatttgct ggggaatctc gttttcttc ttaagacttt tgggacatgg   1200
tttgactccc gaacatcacc gacgcgtctc ctgtttttct gggtggcctc gggacacctg   1260
ccctgccccc acgagggtca ggactgtgac tcttttagg gccaggcagg tgcctggaca   1320
tttgccttgc tggacgggga ctggggatgt gggagggagc agacaggagg aatcatgtca   1380
ggcctgtgtg tgaaaggaag ctccactgtc accctccacc tcttcaccccc ccactcacca   1440 gtgtcccctc cactgtcaca ttgtaactga acttcaggat aataaagtgc ttgcctcc    1498

<210> SEQ ID NO 3
<211> LENGTH: 525
<212> TYPE: DNA
<213> ORGANISM: homo sapiens

<400> SEQUENCE: 3 accccctgg gccctgccag ctccctgccc cagagcttcc tgctcaagtg cttagagcaa     60
gtgaggaaga tccagggcga tggcgcagcg ctccaggaga agctgtgtgc cacctacaag    120
ctgtgccacc ccgaggagct ggtgctgctc ggacactctc tgggcatccc ctgggctccc    180
ctgagcagct gccccagcca ggccctgcag ctggcaggct gcttgagcca actccatagc    240
ggccttttcc tctaccaggg gctcctgcag gccctggaag ggatctcccc cgagttgggt    300
cccaccttgg acacactgca gctggacgtc gccgactttg ccaccaccat ctggcagcag    360
atggaagaac tgggaatggc ccctgccctg cagcccaccc agggtgccat gccggccttc    420
gcctctgctt tccagcgccg ggcaggaggg gtcctagttg cctcccatct gcagagcttc    480
ctggaggtgt cgtaccgcgt tctacgccac cttgcccagc cctga                   525

<210> SEQ ID NO 4
<211> LENGTH: 174
<212> TYPE: PRT
<213> ORGANISM: homo sapiens

<400> SEQUENCE: 4

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
```

-continued

```
            130                 135                 140
Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 5
<211> LENGTH: 863
<212> TYPE: PRT
<213> ORGANISM: homo sapiens

<400> SEQUENCE: 5

Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
                20                  25                  30

Ala Pro Ile Val His Leu Gly Asp Pro Ile Thr Ala Ser Cys Ile Ile
            35                  40                  45

Lys Gln Asn Cys Ser His Leu Asp Pro Glu Pro Gln Ile Leu Trp Arg
    50                  55                  60

Leu Gly Ala Glu Leu Gln Pro Gly Gly Arg Gln Gln Arg Leu Ser Asp
65                  70                  75                  80

Gly Thr Gln Glu Ser Ile Ile Thr Leu Pro His Leu Asn His Thr Gln
                85                  90                  95

Ala Phe Leu Ser Cys Cys Leu Asn Trp Gly Asn Ser Leu Gln Ile Leu
            100                 105                 110

Asp Gln Val Glu Leu Arg Ala Gly Tyr Pro Pro Ala Ile Pro His Asn
        115                 120                 125

Leu Ser Cys Leu Met Asn Leu Thr Thr Ser Ser Leu Ile Cys Gln Trp
    130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
                165                 170                 175

Cys Val Pro Lys Asp Gly Gln Ser His Cys Cys Ile Pro Arg Lys His
            180                 185                 190

Leu Leu Leu Tyr Gln Asn Met Gly Ile Trp Val Gln Ala Glu Asn Ala
        195                 200                 205

Leu Gly Thr Ser Met Ser Pro Gln Leu Cys Leu Asp Pro Met Asp Val
    210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
                245                 250                 255

Gln Pro Gly Leu His Ile Asn Gln Lys Cys Glu Leu Arg His Lys Pro
            260                 265                 270

Gln Arg Gly Glu Ala Ser Trp Ala Leu Val Gly Pro Leu Pro Leu Glu
        275                 280                 285

Ala Leu Gln Tyr Glu Leu Cys Gly Leu Leu Pro Ala Thr Ala Tyr Thr
    290                 295                 300

Leu Gln Ile Arg Cys Ile Arg Trp Pro Leu Pro Gly His Trp Ser Asp
305                 310                 315                 320

Trp Ser Pro Ser Leu Glu Leu Arg Thr Thr Glu Arg Ala Pro Thr Val
                325                 330                 335
```

-continued

```
Arg Leu Asp Thr Trp Trp Arg Gln Arg Gln Leu Asp Pro Arg Thr Val
            340                 345                 350

Gln Leu Phe Trp Lys Pro Val Pro Leu Glu Glu Asp Ser Gly Arg Ile
        355                 360                 365

Gln Gly Tyr Val Val Ser Trp Arg Pro Ser Gly Gln Ala Gly Ala Ile
    370                 375                 380

Leu Pro Leu Cys Asn Thr Thr Glu Leu Ser Cys Thr Phe His Leu Pro
385                 390                 395                 400

Ser Glu Ala Gln Glu Val Ala Leu Val Ala Tyr Asn Ser Ala Gly Thr
                405                 410                 415

Ser Arg Pro Thr Pro Val Val Phe Ser Glu Ser Arg Gly Pro Ala Leu
            420                 425                 430

Thr Arg Leu His Ala Met Ala Arg Asp Pro His Ser Leu Trp Val Gly
        435                 440                 445

Trp Glu Pro Pro Asn Pro Trp Pro Gln Gly Tyr Val Ile Glu Trp Gly
    450                 455                 460

Leu Gly Pro Pro Ser Ala Ser Asn Ser Asn Lys Thr Trp Arg Met Glu
465                 470                 475                 480

Gln Asn Gly Arg Ala Thr Gly Phe Leu Leu Lys Glu Asn Ile Arg Pro
                485                 490                 495

Phe Gln Leu Tyr Glu Ile Ile Val Thr Pro Leu Tyr Gln Asp Thr Met
            500                 505                 510

Gly Pro Ser Gln His Val Tyr Ala Tyr Ser Gln Glu Met Ala Pro Ser
        515                 520                 525

His Ala Pro Glu Leu His Leu Lys His Ile Gly Lys Thr Trp Ala Gln
    530                 535                 540

Leu Glu Trp Val Pro Glu Pro Pro Glu Leu Gly Lys Ser Pro Leu Thr
545                 550                 555                 560

His Tyr Thr Ile Phe Trp Thr Asn Ala Gln Asn Gln Ser Phe Ser Ala
                565                 570                 575

Ile Leu Asn Ala Ser Ser Arg Gly Phe Val Leu His Gly Leu Glu Pro
            580                 585                 590

Ala Ser Leu Tyr His Ile His Leu Met Ala Ala Ser Gln Ala Gly Ala
        595                 600                 605

Thr Asn Ser Thr Val Leu Thr Leu Met Thr Leu Thr Pro Glu Gly Ser
    610                 615                 620

Glu Leu His Ile Ile Leu Gly Leu Phe Gly Leu Leu Leu Leu Leu Thr
625                 630                 635                 640

Cys Leu Cys Gly Thr Ala Trp Leu Cys Cys Ser Pro Asn Arg Lys Asn
                645                 650                 655

Pro Leu Trp Pro Ser Val Pro Asp Pro Ala His Ser Ser Leu Gly Ser
            660                 665                 670

Trp Val Pro Thr Ile Met Glu Glu Leu Pro Gly Pro Arg Gln Gly Gln
        675                 680                 685

Trp Leu Gly Gln Thr Ser Glu Met Ser Arg Ala Leu Thr Pro His Pro
    690                 695                 700

Cys Val Gln Asp Ala Phe Gln Leu Pro Gly Leu Gly Thr Pro Pro Ile
705                 710                 715                 720

Thr Lys Leu Thr Val Leu Glu Glu Asp Glu Lys Lys Pro Val Pro Trp
                725                 730                 735

Glu Ser His Asn Ser Ser Glu Thr Cys Gly Leu Pro Thr Leu Val Gln
            740                 745                 750

Thr Tyr Val Leu Gln Gly Asp Pro Arg Ala Val Ser Thr Gln Pro Gln
```

|  | 755 |  |  |  | 760 |  |  |  | 765 |  |  |
|---|---|---|---|---|---|---|---|---|---|---|---|

Ser Gln Ser Gly Thr Ser Asp Gln Val Leu Tyr Gly Gln Leu Leu Gly
            770                 775                 780

Ser Pro Thr Ser Pro Gly Pro Gly His Tyr Leu Arg Cys Asp Ser Thr
785                 790                 795                 800

Gln Pro Leu Leu Ala Gly Leu Thr Pro Ser Pro Lys Ser Tyr Glu Asn
            805                 810                 815

Leu Trp Phe Gln Ala Ser Pro Leu Gly Thr Leu Val Thr Pro Ala Pro
            820                 825                 830

Ser Gln Glu Asp Asp Cys Val Phe Gly Pro Leu Leu Asn Phe Pro Leu
            835                 840                 845

Leu Gln Gly Ile Arg Val His Gly Met Glu Ala Leu Gly Ser Phe
            850                 855                 860

<210> SEQ ID NO 6
<211> LENGTH: 3024
<212> TYPE: DNA
<213> ORGANISM: homo sapiens

<400> SEQUENCE: 6

| gaagctggac tgcagctggt ttcaggaact tctcttgacg agaagagaga ccaaggaggc | 60 |
|---|---|
| caagcagggg ctgggccaga ggtgccaaca tggggaaact gaggctcggc tcggaaaggt | 120 |
| gaagtaactt gtccaagatc acaaagctgg tgaacatcaa gttggtgcta tggcaaggct | 180 |
| gggaaactgc agcctgactt gggctgccct gatcatcctg ctgctccccg aagtctgga | 240 |
| ggagtgcggg cacatcagtg tctcagcccc catcgtccac ctgggggatc ccatcacagc | 300 |
| ctcctgcatc atcaagcaga actgcagcca tctggacccg agccacaga ttctgtggag | 360 |
| actgggagca gagcttcagc ccgggggcag gcagcagcgt ctgtctgatg ggacccagga | 420 |
| atctatcatc ccctgcccc acctcaacca cactcaggcc tttctctcct gctgcctgaa | 480 |
| ctggggcaac agcctgcaga tcctggacca ggttgagctg cgcgcaggct accctccagc | 540 |
| catacccac aacctctcct gcctcatgaa cctcacaacc agcagcctca tctgccagtg | 600 |
| ggagccagga cctgagaccc acctaccac cagcttcact ctgaagagtt tcaagagccg | 660 |
| gggcaactgt cagacccaag gggactccat cctggactgc gtgcccaagg acgggcagag | 720 |
| ccactgctgc atcccacgca aacacctgct gttgtaccag aatatgggca tctgggtgca | 780 |
| ggcagagaat gcgctgggga ccagcatgtc cccacaactg tgtcttgatc ccatggatgt | 840 |
| tgtgaaactg gagcccccca tgctgcggac catggacccc agccctgaag cggcccctcc | 900 |
| ccaggcaggc tgcctacagc tgtgctggga gccatggcag ccaggcctgc acataaatca | 960 |
| gaagtgtgag ctgcgccaca gccgcagcg tggagaagcc agctgggcac tggtgggccc | 1020 |
| cctcccttg gaggccctc agtatgagct ctgcgggctc ctcccagcca cggcctacac | 1080 |
| cctgcagata cgctgcatcc gctggcccct gcctggccac tggagcgact ggagccccag | 1140 |
| cctggagctg agaactaccg aacgggcccc cactgtcaga ctggacacat ggtggcggca | 1200 |
| gaggcagctg accccagga cagtgcagct gttctggaag ccagtgcccc tggaggaaga | 1260 |
| cagcggacgg atccaaggtt atgtggtttc ttggagaccc tcaggccagg ctggggccat | 1320 |
| cctgccctc tgcaacacca cagagctcag ctgcaccttc cacctgcctt cagaagccca | 1380 |
| ggaggtggcc cttgtggcct ataactcagc cgggacctct cgccccaccc cggtggtctt | 1440 |
| ctcagaaagc agaggcccag ctctgaccag actccatgcc atggcccgag accctcacag | 1500 |
| cctctgggta ggctgggagc cccccaatcc atggcctcag ggctatgtga ttgagtgggg | 1560 |

```
cctgggcccc cccagcgcga gcaatagcaa caagacctgg aggatggaac agaatgggag    1620
agccacgggg tttctgctga aggagaacat caggcccttt cagctctatg agatcatcgt    1680
gactcccttg taccaggaca ccatgggacc ctcccagcat gtctatgcct actctcaaga    1740
aatggctccc tcccatgccc cagagctgca tctaaagcac attggcaaga cctgggcaca    1800
gctggagtgg gtgcctgagc cccctgagct ggggaagagc ccccttaccc actacaccat    1860
cttctggacc aacgctcaga accagtcctt ctccgccatc ctgaatgcct cctcccgtgg    1920
ctttgtcctc catggcctgg agcccgccag tctgtatcac atccacctca tggctgccag    1980
ccaggctggg gccaccaaca gtacagtcct caccctgatg accttgaccc cagaggggtc    2040
ggagctacac atcatcctgg gcctgttcgg cctcctgctg ttgctcacct gcctctgtgg    2100
aactgcctgg ctctgttgca gccccaacag gaagaatccc ctctggccaa gtgtcccaga    2160
cccagctcac agcagcctgg gctcctgggt gcccacaatc atggaggagc tgcccggacc    2220
cagacaggga cagtgctggg gcagacatc tgaaatgagc cgtgctctca ccccacatcc    2280
ttgtgtgcag gatgccttcc agctgcccgg ccttggcacg ccacccatca ccaagctcac    2340
agtgctggag gaggatgaaa agaagccggt gccctgggag tcccataaca gctcagagac    2400
ctgtggcctc cccactctgg tccagaccta tgtgctccag ggggacccaa gagcagtttc    2460
cacccagccc caatcccagt ctggcaccag cgatcaggtc ctttatgggc agctgctggg    2520
cagccccaca agcccagggc cagggcacta tctccgctgt gactccactc agcccctctt    2580
ggcgggcctc acccccagcc caagtcctta tgagaacctc tggttccagg ccagcccctt    2640
ggggaccctg gtaaccccag ccccaagcca ggaggacgac tgtgtctttg gccactgct    2700 caacttcccc ctcctgcagg ggatccgggt ccatgggatg gaggcgctgg ggagcttcta    2760
gggcttcctg gggttccctt cttgggcctg cctcttaaag gcctgagcta gctggagaag    2820
aggggagggt ccataagccc atgactaaaa actaccccag cccaggctct caccatctcc    2880
agtcaccagc atctccctct cctcccaatc tccataggct gggcctccca ggcgatctgc    2940
atactttaag gaccagatca tgctccatcc agccccaccc aatggccttt tgtgcttgtt    3000
tcctataact tcagtattgt aaac                                           3024

<210> SEQ ID NO 7
<211> LENGTH: 2520
<212> TYPE: DNA
<213> ORGANISM: homo sapiens

<400> SEQUENCE: 7
gagtgcgggc acatcagtgt ctcagccccc atcgtccacc tggggatcc catcacagcc       60 tcctgcatca tcaagcagaa ctgcagccat ctggacccgg agccacagat tctgtggaga      120
ctgggagcag agcttcagcc cgggggcagg cagcagcgtc tgtctgatgg acccaggaa      180 tctatcatca ccctgcccca cctcaaccac actcaggcct ttctctcctg ctgcctgaac      240
tggggcaaca gcctgcagat cctggaccag gttgagctgc gcgcaggcta ccctccagcc      300
ataccccaca acctctcctg cctcatgaac ctcacaacca gcagcctcat ctgccagtgg      360
gagccaggac ctgagaccca cctacccacc agcttcactc tgaagagttt caagagccgg      420
ggcaactgtc agacccaagg ggactccatc ctggactgcg tgcccaagga cgggcagagc      480
cactgctgca tccacgcaa acacctgctg ttgtaccaga atatgggcat ctgggtgcag      540
gcagagaatg cgctggggac cagcatgtcc ccacaactgt gtcttgatcc catggatgtt      600
```

```
gtgaaactgg agccccccat gctgcggacc atggacccca gccctgaagc ggcccctccc      660
caggcaggct gcctacagct gtgctgggag ccatggcagc caggcctgca cataaatcag      720
aagtgtgagc tgcgccacaa gccgcagcgt ggagaagcca gctgggcact ggtgggcccc      780
ctccccttgg aggcccttca gtatgagctc tgcgggctcc tcccagccac ggcctacacc      840
ctgcagatac gctgcatccg ctggcccctg cctggccact ggagcgactg gagccccagc      900
ctggagctga gaactaccga acgggccccc actgtcagac tggacacatg gtggcggcag      960
aggcagctgg accccaggac agtgcagctg ttctggaagc cagtgcccct ggaggaagac     1020
agcggacgga tccaaggtta tgtggttttct tggagaccct caggccaggc tggggccatc     1080
ctgcccctct gcaacaccac agagctcagc tgcaccttcc acctgccttc agaagcccag     1140
gaggtggccc ttgtggccta taactcagcc gggacctctc gccccacccc ggtggtcttc     1200
tcagaaagca gaggcccagc tctgaccaga ctccatgcca tggcccgaga ccctcacagc     1260
ctctgggtag gctgggagcc cccaatcca tggcctcagg gctatgtgat tgagtggggc      1320
ctgggccccc cagcgcgag caatagcaac aagacctgga ggatgaaaca gaatgggaga      1380 gccacgggt ttctgctgaa ggagaacatc aggccctttc agctctatga gatcatcgtg      1440
actcccttgt accaggacac catgggaccc tcccagcatg tctatgccta ctctcaagaa     1500
atggctccct cccatgcccc agagctgcat ctaaagcaca ttggcaagac ctgggcacag     1560
ctggagtggg tgcctgagcc ccctgagctg ggaagagcc cccttaccca ctacaccatc     1620
ttctggacca acgctcagaa ccagtccttc tccgccatcc tgaatgcctc ctcccgtggc     1680
tttgtcctcc atggctgga gcccgccagt ctgtatcaca tccacctcat ggctgccagc     1740
caggctgggg ccaccaacag tacagtcctc accctgatga ccttgacccc agaggggtcg     1800
gagctacaca tcatcctggg cctgttcggc ctcctgctgt tgctcacctg cctctgtgga     1860
actgcctggc tctgttgcag ccccaacagg aagaatcccc tctggccaag tgtcccagac     1920
ccagctcaca gcagcctggg ctcctgggtg cccacaatca tggaggagct gcccggaccc     1980
agacagggac agtggctggg gcagacatct gaaatgagcc gtgctctcac cccacatcct     2040
tgtgtgcagg atgccttcca gctgcccggc cttggcacgc cacccatcac caagctcaca     2100
gtgctggagg aggatgaaaa gaagccggtg ccctgggagt cccataacag ctcagagacc     2160 tgtgcctcc ccactctggt ccagacctat gtgctccagg ggacccaag agcagtttcc      2220 acccagcccc aatcccagtc tggcaccagc gatcaggtcc tttatgggca gctgctgggc     2280
agccccacaa gccagggcc agggcactat ctccgctgtg actccactca gcccctcttg      2340
gcgggcctca ccccagccc caagtcctat gagaacctct ggttccaggc cagccccttg     2400
gggaccctgg taaccccagc cccaagccag gaggacgact gtgtctttgg ccactgctc      2460 aacttccccc tcctgcaggg gatccgggtc catgggatgg aggcgctggg gagcttctag     2520
```

<210> SEQ ID NO 8
<211> LENGTH: 839
<212> TYPE: PRT
<213> ORGANISM: homo sapiens

<400> SEQUENCE: 8

Glu Cys Gly His Ile Ser Val Ser Ala Pro Ile Val His Leu Gly Asp
1               5                   10                  15

Pro Ile Thr Ala Ser Cys Ile Ile Lys Gln Asn Cys Ser His Leu Asp
            20                  25                  30

Pro Glu Pro Gln Ile Leu Trp Arg Leu Gly Ala Glu Leu Gln Pro Gly

```
                35                  40                  45
Gly Arg Gln Gln Arg Leu Ser Asp Gly Thr Gln Glu Ser Ile Ile Thr
 50                  55                  60
Leu Pro His Leu Asn His Thr Gln Ala Phe Leu Ser Cys Cys Leu Asn
 65                  70                  75                  80
Trp Gly Asn Ser Leu Gln Ile Leu Asp Gln Val Glu Leu Arg Ala Gly
                 85                  90                  95
Tyr Pro Pro Ala Ile Pro His Asn Leu Ser Cys Leu Met Asn Leu Thr
            100                 105                 110
Thr Ser Ser Leu Ile Cys Gln Trp Glu Pro Gly Pro Glu Thr His Leu
            115                 120                 125
Pro Thr Ser Phe Thr Leu Lys Ser Phe Lys Ser Arg Gly Asn Cys Gln
130                 135                 140
Thr Gln Gly Asp Ser Ile Leu Asp Cys Val Pro Lys Asp Gly Gln Ser
145                 150                 155                 160
His Cys Cys Ile Pro Arg Lys His Leu Leu Leu Tyr Gln Asn Met Gly
                165                 170                 175
Ile Trp Val Gln Ala Glu Asn Ala Leu Gly Thr Ser Met Ser Pro Gln
            180                 185                 190
Leu Cys Leu Asp Pro Met Asp Val Val Lys Leu Glu Pro Pro Met Leu
            195                 200                 205
Arg Thr Met Asp Pro Ser Pro Glu Ala Ala Pro Pro Gln Ala Gly Cys
210                 215                 220
Leu Gln Leu Cys Trp Glu Pro Trp Gln Pro Gly Leu His Ile Asn Gln
225                 230                 235                 240
Lys Cys Glu Leu Arg His Lys Pro Gln Arg Gly Glu Ala Ser Trp Ala
                245                 250                 255
Leu Val Gly Pro Leu Pro Leu Glu Ala Leu Gln Tyr Glu Leu Cys Gly
            260                 265                 270
Leu Leu Pro Ala Thr Ala Tyr Thr Leu Gln Ile Arg Cys Ile Arg Trp
            275                 280                 285
Pro Leu Pro Gly His Trp Ser Asp Trp Ser Pro Ser Leu Glu Leu Arg
            290                 295                 300
Thr Thr Glu Arg Ala Pro Thr Val Arg Leu Asp Thr Trp Trp Arg Gln
305                 310                 315                 320
Arg Gln Leu Asp Pro Arg Thr Val Gln Leu Phe Trp Lys Pro Val Pro
                325                 330                 335
Leu Glu Glu Asp Ser Gly Arg Ile Gln Gly Tyr Val Val Ser Trp Arg
            340                 345                 350
Pro Ser Gly Gln Ala Gly Ala Ile Leu Pro Leu Cys Asn Thr Thr Glu
            355                 360                 365
Leu Ser Cys Thr Phe His Leu Pro Ser Glu Ala Gln Glu Val Ala Leu
            370                 375                 380
Val Ala Tyr Asn Ser Ala Gly Thr Ser Arg Pro Thr Pro Val Val Phe
385                 390                 395                 400
Ser Glu Ser Arg Gly Pro Ala Leu Thr Arg Leu His Ala Met Ala Arg
                405                 410                 415
Asp Pro His Ser Leu Trp Val Gly Trp Glu Pro Asn Pro Trp Pro
            420                 425                 430
Gln Gly Tyr Val Ile Glu Trp Gly Leu Gly Pro Pro Ser Ala Ser Asn
            435                 440                 445
Ser Asn Lys Thr Trp Arg Met Glu Gln Asn Gly Arg Ala Thr Gly Phe
450                 455                 460
```

```
Leu Leu Lys Glu Asn Ile Arg Pro Phe Gln Leu Tyr Glu Ile Ile Val
465                 470                 475                 480

Thr Pro Leu Tyr Gln Asp Thr Met Gly Pro Ser Gln His Val Tyr Ala
            485                 490                 495

Tyr Ser Gln Glu Met Ala Pro Ser His Ala Pro Glu Leu His Leu Lys
        500                 505                 510

His Ile Gly Lys Thr Trp Ala Gln Leu Glu Trp Val Pro Glu Pro Pro
    515                 520                 525

Glu Leu Gly Lys Ser Pro Leu Thr His Tyr Thr Ile Phe Trp Thr Asn
530                 535                 540

Ala Gln Asn Gln Ser Phe Ser Ala Ile Leu Asn Ala Ser Ser Arg Gly
545                 550                 555                 560

Phe Val Leu His Gly Leu Glu Pro Ala Ser Leu Tyr His Ile His Leu
            565                 570                 575

Met Ala Ala Ser Gln Ala Gly Ala Thr Asn Ser Thr Val Leu Thr Leu
        580                 585                 590

Met Thr Leu Thr Pro Glu Gly Ser Glu Leu His Ile Ile Leu Gly Leu
    595                 600                 605

Phe Gly Leu Leu Leu Leu Leu Thr Cys Leu Cys Gly Thr Ala Trp Leu
610                 615                 620

Cys Cys Ser Pro Asn Arg Lys Asn Pro Leu Trp Pro Ser Val Pro Asp
625                 630                 635                 640

Pro Ala His Ser Ser Leu Gly Ser Trp Val Pro Thr Ile Met Glu Glu
            645                 650                 655

Leu Pro Gly Pro Arg Gln Gly Gln Trp Leu Gly Gln Thr Ser Glu Met
        660                 665                 670

Ser Arg Ala Leu Thr Pro His Pro Cys Val Gln Asp Ala Phe Gln Leu
    675                 680                 685

Pro Gly Leu Gly Thr Pro Pro Ile Thr Lys Leu Thr Val Leu Glu Glu
690                 695                 700

Asp Glu Lys Lys Pro Val Pro Trp Glu Ser His Asn Ser Ser Glu Thr
705                 710                 715                 720

Cys Gly Leu Pro Thr Leu Val Gln Thr Tyr Val Leu Gln Gly Asp Pro
            725                 730                 735

Arg Ala Val Ser Thr Gln Pro Gln Ser Gln Ser Gly Thr Ser Asp Gln
        740                 745                 750

Val Leu Tyr Gly Gln Leu Leu Gly Ser Pro Thr Ser Pro Gly Pro Gly
    755                 760                 765

His Tyr Leu Arg Cys Asp Ser Thr Gln Pro Leu Leu Ala Gly Leu Thr
770                 775                 780

Pro Ser Pro Lys Ser Tyr Glu Asn Leu Trp Phe Gln Ala Ser Pro Leu
785                 790                 795                 800

Gly Thr Leu Val Thr Pro Ala Pro Ser Gln Glu Asp Asp Cys Val Phe
            805                 810                 815

Gly Pro Leu Leu Asn Phe Pro Leu Leu Gln Gly Ile Arg Val His Gly
        820                 825                 830

Met Glu Ala Leu Gly Ser Phe
    835
```

TREATMENT OF NEUROLOGICAL CONDITIONS

This application is associated with and claims priority from U.S. Provisional Patent Application No. 61/242,503, filed on 15 Sep. 2009 entitled "Treatment of neurological conditions", the entire contents of which, are incorporated herein by reference.

FIELD

The present invention relates generally to a method for treating or preventing or otherwise ameliorating the effects of an inflammatory neurodegenerative condition of the central nervous system (CNS) and in particular multiple sclerosis, Devic's disease or a viral infection and symptoms and complications arising therefrom.

BACKGROUND

Bibliographic details of references provided in the subject specification are listed at the end of the specification.

Reference to any prior art is not, and should not be taken as an acknowledgment or any form of suggestion that this prior art forms part of the common general knowledge in any country.

Multiple sclerosis (MS) and Devic's disease (also known as Neuromyelitis Optica [NMO]) are inflammatory neurodegenerative disorders that affect the central nervous system (CNS). They are caused by autoimmune attack in which inflammatory cells invade the nervous system leading to demyelination and tissue destruction (Morales et al, *Adv Neurol* 98:27-45, 2006). This destruction and demyelination leads to impairment of cognitive function and higher mortality (Bergamaschi et al, *Neuroepidemiology* 25 (1):15-8, 2005; Ragonese et al, *Eur J Neurol* 15 (2):123-7, 2008). MS is more common in women than men, affecting approximately 3 people per 100,000 (Alonso et al, *Neurology* 71 (2):129-35, 2008) and can be categorized into either relapsing remitting (majority of cases) or rapidly progressing (minority [10%]) forms. Currently, there is no cure for either form of the disease. Standard therapies for neurological inflammation include recombinant interferon treatment and immunosuppressive agents such as methylprednisolone or methotrexate (Lopez-Diego et al, *Nat Rev Drug Discov* 7 (11):909-25, 2008). These treatments reduce but do not prevent progression of the disease. There is a need to develop an efficacious treatment.

MS lesions are characterized by infiltration by a range of immune cells including T cells, macrophages, dendritic cells and neutrophils (Morales et al, 2006 supra). Similar lesions are also found in Devic's disease patients that are often more aggressive and rapidly progressing with preferential involvement of the spinal cord and optic nerves (Wingerchuk et al, *Lancet Neurol* 6 (9):805-15, 2007; Wingerchuk et al, *Curr Treat Options Neurol* 10 (1):55-66, 2008). Although both disorders are widely believed to be the result of aberrant CD4+ helper T cell responses, T cell targeted therapies have been relatively unsuccessful in the clinic (Lopez-Diego et al, 2008 supra). This has led to a renewed focused on the role of innate immune cells in neurological pathologies (Weiner et al, *J Neurol* 255 (Suppl 1): 3-11, 2008).

Neutrophils are one of the central innate immune effector cells and are rapidly recruited to sites of inflammation where they release damaging agents such as reactive oxygen metabolites. They can be found along with other immune cells infiltrating the nervous system in both MS and Devic's disease patients. Lesional tissue and cerebrospinal fluid from Devic's disease patients (who have often been diagnosed as having a poor prognosis) are particularly neutrophil rich (Wingerchuk et al, 2007; 2008; supra). However, the role of neutrophils in CNS pathologies remains unclear. Neutrophils have been suggested in the literature as having either a protective role or a pathogenic role in animal models of CNS autoimmune inflammation. Depleting neutrophils with a neutrophil specific monoclonal antibody in a mouse model of MS reduced disease severity (McColl et al, *J Immunol* 161 (11): 6421-6, 1998). On the other hand, other researchers investigating neutrophils in a mouse model of MS found that neutrophils isolated from the CNS are effective T cell suppressors (Zehntner et al, *J Immunol* 174 (8):5124-31, 2005).

One cytokine involved in inflammatory reactions is granulocyte colony-stimulating factor (G-CSF) which is encoded by the CSF-3 gene. G-CSF is a hemopoietic growth factor that regulates the production of granulocytes (Nicola et al, *Nature* 314:625, 1985; Metcalf, *International Journal of Cancer* 25:225, 1980; Nicola et al, *Journal of Biological Chemistry* 258:9017, 1983). G-CSF mediates its effects through interaction with the G-CSF receptor (G-CSFR, encoded by the CSFR-3 gene), a member of the type I cytokine receptor superfamily (Demetri et al, *Blood* 78:2791-2808, 1991). Major biological actions of G-CSF in humans and mice include increasing the production and release of neutrophils from the bone marrow (Souza et al, *Science* 232:61, 1986; Lord et al, *Proc. Natl. Acad. Sci. USA* 86:9499-9503, 1989), mobilizing hemopoietic progenitor cells from the marrow into the peripheral blood (Bungart et al, *British Journal of Haematology* 22:1156, 1990; de Haan et al, *Blood* 86:2986-2992, 1995; Roberts et al, *Blood* 89:2736-2744, 1997) and modulating the differentiation and effector functions of mature neutrophils (Yong et al, *European Journal of Haematology* 49:251-259, 1992; Colotta et al, *Blood* 80:2012-2020, 1992; Rex et al, *Transfusion* 35:605-611, 1995; Gericke et al, *Journal of Leukocyte Biology* 57:455-461, 1995; Xu et al, *British Journal of Haematology* 93:558-568, 1996; Yong, *British Journal of Haematology* 94:40-47, 1996; Jacob et al, *Blood* 92:353-361, 1998). G-CSF also acts on mature postmitotic neutrophils after they leave the bone marrow including having effects on phagocytosis (Bialek et al, *Infection* 26 (6):375-8, 1998), apoptosis (Dibbert et al, *Proc Natl Acad Sci USA* 96 (23):13330-5, 1999) and homing (Dagia et al, *Nat Med* 12 (10):1185-90, 2006; Eyles et al, *Blood* 112 (13): 5193-201, 2008). G-CSF is used to treat neutropenia, as well as to induce mobilization of hemopoietic stem cells (HSC) for autologous and allogenic stem cell transplantation (Welte et al, *Blood* 88:1907-1929, 1996).

As outlined above, there is experimental evidence with neutrophil depleting antibodies that support a pro-inflammatory function for the G-CSF/neutrophil axis in MS. In addition, clinical case studies have reported that some patients treated with G-CSF display a worsening of clinical symptoms (Openshaw et al, "*Neurology* 54 (11):2147-50, 2000; Snir et al, *J Neuroimmunol* 172 (1-2):145-55, 2006). However, these reports are relatively rare and significant evidence exists supporting an anti-inflammatory role for G-CSF in CNS disease conditions. In the experimental autoimmune encephalomyelitis (EAE) animal model of MS, treatment with systemic and local (CNS) delivered G-CSF alleviates disease (Zavala et al, *J Immunol* 168 (4):2011-9, 2002). This is consistent with the T cell tolerizing (Rutella et al, *Transplantation* 84 (1 Suppl):S26-30, 2007) and neuroprotective role (Frank et al, *BMC Neurosci* 10:49, 2009) prescribed to G-CSF by others. In addition, the anti-inflammatory properties of G-CSF have been well documented in other autoimmune diseases such as type I diabetes (Hadaya et al, *J Autoimmun* 24 (2):125-34, 2005) and inflammatory bowel disease (Kudo et al, *Scand J Gastroenterol* 43 (6):689-97, 2008). In fact, recombinant human G-CSF has even been used in the clinic to treat inflammatory bowel disease (Barahona-Gamido et al, *Biologics* 2 (3):501-4, 2008). Hence, G-CSF is a pleiotropic cytokine having a multiplicity of roles.

There is a need to develop new treatments for inflammatory neurodegenerative conditions in the CNS such as MS, Devic's disease and viral infections of the brain.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present invention relates generally to the use of antagonists of G-CSF, its receptor and/or their production in the treatment of inflammatory neurodegenerative conditions, including disease conditions, of the CNS. Generally, the inflammatory neurodegenerative conditions are associated with infiltration of neutrophils. In particular, the present invention contemplates the treatment of multiple sclerosis (MS), Devic's disease (also known as neuromyelitis optica or NMO) and viral infection by antagonizing G-CSF, its receptor or their production.

The present invention contemplates, therefore, the inhibition of G-CSF or G-CSFR systemically or locally and/or the down-regulation of expression of a G-CSF or G-CSFR in the treatment of inflammatory neurodegenerative conditions. As indicated above, the neurodegenerative conditions are generally those associated with infiltration of neutrophils such as MS, Devic's disease and a viral infection.

Reference to "G-CSF" or its full name "granulocyte-colony stimulating factor" includes homologs and derivatives of G-CSF. A "homolog" or "derivative" includes polymorphic variants of G-CSF.

The term "G-CSFR" or its full name "granulocyte-colony stimulating factor receptor" includes homologs and derivatives of G-CSFR. A "homolog" or "derivative" includes polymorphic variants of G-CSF.

By "down regulating expression of G-CSF or G-CSFR" includes inhibiting expression of genetic material encoding G-CSF or G-CSFR including inhibiting transcription, translation and/or mRNA processing.

The expression "inhibition of G-CSF or G-CSFR" or "antagonizing G-CSF or G-CSFR" includes inhibiting the activity or signaling function of G-CSF or G-CSFR.

An inflammatory neurodegenerative condition of the CNS includes a disease condition. Generally, the condition is characterized by or associated with infiltration of neutrophils. Examples include MS, Devic's disease and a viral infection.

Accordingly, one aspect of the present invention contemplates a method for the treatment of an inflammatory neurodegenerative condition of the CNS in a subject, the method comprising administering to the subject an amount of an agent effective to inhibit G-CSF or G-CSFR or down regulate expression of G-CSF or G-CSFR.

In a particular embodiment, the present invention provides a method for treating an inflammatory neurodegenerative condition of the CNS in a subject, said method comprising administering to said subject a G-CSF or G-CSFR inhibiting agent selected from the group consisting of an antibody specific for G-CSF or G-CSFR; a soluble G-CSFR or a G-CSF-binding portion thereof and a 20 to 30 nucleotide sense or antisense molecule targeted to a nucleic acid molecule encoding G-CSF, the nucleic acid molecule comprising the sequence set forth in SEQ ID NO:3 or a 20 to 30 nucleotide sense or antisense molecule targeted to a nucleic acid molecule encoding a G-CSFR, the nucleic acid molecule comprising the sequence set forth in SEQ ID NO:7.

A method is hence provided for treating an inflammatory neurodegenerative condition of the CNS in a subject, the method comprising administering to the subject an agent which inhibits G-CSF or G-CSFR or down regulates expression of G-CSF or G-CSFR, the agent selected from the group consisting of:

a. an antibody specific for G-CSF or G-CSFR;
b. a soluble G-CSFR or a G-CSF-binding portion thereof;
c. a 20 to 30 nucleotide sense or antisense molecule targeted to a nucleic acid molecule encoding G-CSF, the nucleic acid molecule comprising the sequence set forth in SEQ ID NO:3; or a 20 to 30 nucleotide sense or antisense molecule targeted to a nucleic acid molecule encoding a G-CSFR, the nucleic acid molecule comprising the sequence set forth in SEQ ID NO:7.

Generally, the agent is administered for a time and under conditions sufficient to ameliorate the symptoms of the inflammatory neurodegenerative condition of the CNS. Generally, the condition is associated with infiltration of neutrophils such as MS, Devic's disease or a viral infection.

More particularly, the present invention is directed to a method for the treatment of MS, Devic's disease or a viral infection in a subject the method comprising administering to the subject an amount of an agent effective to inhibit G-CSF or G-CSFR or inhibit expression of G-CSF or G-CSFR.

The administration may be systemic or local. Systemic administration is particularly useful. Reference to "systemic administration" includes intra-articular, intravenous, intramuscular, intraperitoneal, and subcutaneous injection, infusion, as well as administration via oral, rectal and nasal routes, or via inhalation. Administration by intravenous or subcutaneous injection is particularly useful.

The agents which antagonize G-CSF, G-CSFR or their production include proteinaceous, non-proteinaceous (e.g. chemical entities) and nucleic acid molecules.

Proteinaceous and non-proteinaceous molecules include peptides, polypeptides and proteins, small, intermediate or large chemical molecules as well as molecules identified from natural product screening or the screening of chemical libraries. Natural product screening includes the screening of extracts or samples from plants, microorganisms, soil river beds, coral, aquatic environments and extraterrestrial environments for molecules or groups of molecules which effect G-CSF or G-CSFR activity or the level of G-CSF or G-CSFR expression. These molecules may also affect G-CSF/G-CSFR interaction or otherwise modulate G-CSF/G-CSFR-mediated signaling.

The present invention further contemplates combination therapy such as antagonizing G-CSF and/or G-CSFR in combination with another anti-inflammatory agent, immunosuppressive agent or other agent used in the treatment of an inflammatory neurodegenerative condition of the CNS.

Accordingly, another aspect of the present invention relates to a method for the treatment of an inflammatory neurodegenerative condition of the CNS such as but not limited to MS, Devic's disease or a viral infection in a subject, the method comprising administering an agent which inhibits G-CSF or G-CSFR or inhibits the expression of G-CSF or G-CSFR and at least one other therapeutic agent such as an anti-inflammatory such as corticosteroids, an immunosuppressives such as mitoxantrone, glatiramer acetate, interferons, or chemotherapeutic agents.

One particular G-CSF or G-CSFR antagonizing agent is an antibody which inhibits the activity of G-CSF or G-CSFR. In an embodiment, the antibody specifically or selectively binds to G-CSF or G-CSFR. Other useful agents include small molecule inhibitors, soluble G-CSF receptors or G-CSF-binding fragments thereof, receptor-binding portions of G-CSF and nucleic acid molecules which inhibit G-CSF or G-CSFR expression. The antibody may be mono-specific or multi-specific including bi-specific.

Hence, in an embodiment, the present invention contemplates a method for the treatment of MS, Devic's disease or a viral infection in the brain in a subject, the method comprising administering to the subject an amount of an antibody effective to inhibit the activity of G-CSF or G-CSFR or the ability for G-CSF to interact with G-CSFR. This aspect of the present invention includes the administration of an antibody effective to inhibit G-CSF/G-CSFR-mediated signaling.

Whilst sense or antisense molecules directed to the G-CSF gene or mRNA or G-CSFR gene or mRNA are provided, sense or antisense molecules are also provided against any portion of the coding or non-coding regions including leader sequence and selected introns or extons of the G-CSF or G-CSFR gene or mRNA. Hence, sense and antisense molecules of 20 to 30 nucleotides in length are contemplated herein to one or more of SEQ ID NOs:2, 3, 6 and/or 7.

Useful subjects to be treated are mammals and in particular humans.

The present invention extends to the use of pharmaceutical compositions comprising antagonists of G-CSF or G-CSFR. One particularly useful composition comprises an anti-G-CSF antibody or an anti-G-CSFR antibody. As indicated above, an antagonist of G-CSF or G-CSFR includes an antagonist of G-CSF or G-CSFR activity.

The present invention further contemplates the use of an antibody to G-CSF or G-CSFR in the manufacture of a medicament for the treatment of MS, Devic's disease or a viral infection in the brain in a subject.

Another aspect provides for the use of an agent which inhibits G-CSF or G-CSFR or which inhibits expression of G-CSF or G-CSFR in the manufacture of a medicament for treating an inflammatory neurodegenerative condition of the CNS in a subject, wherein the agent is selected from the group consisting of:

a. an antibody specific for G-CSF or G-CSFR;

b. a soluble G-CSFR or a G-CSF-binding portion thereof;

c. a 20 to 30 nucleotide sense or antisense molecule targeted to a nucleic acid molecule encoding G-CSF, the nucleic acid molecule comprising the sequence set forth in SEQ ID NO:3; or a 20 to 30 nucleotide sense or antisense molecule targeted to a nucleic acid molecule encoding a G-CSFR, the nucleic acid molecule comprising the sequence set forth in SEQ ID NO:7.

A summary of sequence identifiers used throughout the subject specification is provided in Table 1. A list of abbreviations is provided in Table 2.

TABLE 1

Summary of sequence identifiers

| Sequence ID No. | Description |
|---|---|
| 1 | Human G-CSF amino acid sequence including the leader sequence |
| 2 | Human G-CSF coding and non-coding nucleotide sequence |
| 3 | Human G-CSF nucleotide sequence encoding mature protein |
| 4 | Human G-CSF mature protein amino acid sequence |
| 5 | Human G-CSFR3 amino acid sequence including the leader sequence |
| 6 | Human G-CSF3R coding and non-coding nucleotide sequence |
| 7 | Human G-CSF3R nucleotide sequence encoding mature protein |
| 8 | Human G-CSF3R mature protein amino acid sequence |

TABLE 2

Abbreviations

| Abbreviation | Description |
|---|---|
| CNS | Central nervous system |
| EAE | Experimental immune encephalomyelitis |
| G-CSF | Granulocyte-colony stimulating factor |
| G-CSFR | Granulocyte-colony stimulating factor receptor |
| MS | Multiple sclerosis |
| NMO | Neuromyelitis optica (also known as Devic's Disease) |

DETAILED DESCRIPTION

Figure 1:
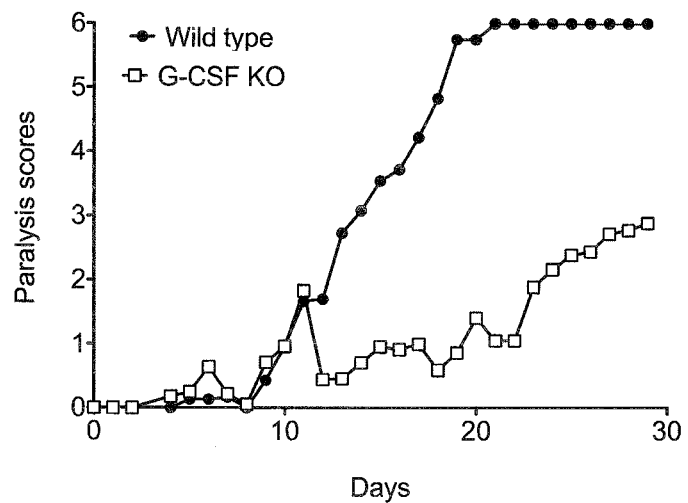
FIG. 1 is a graphical representation showing that G-CSF deficient mice are protected from experimental autoimmune encephalomyelitis (EAE) compared to wild type (C57Bl/6) mice. Disease was monitored from day 0 to 30 and paralysis scores determined as noted in the experimental section.

The singular forms "a", "an" and "the" include plural aspects unless the context clearly dictates otherwise. Thus, for example, reference to "a neurodegenerative condition" includes a single condition as well as two or more conditions; reference to "an agent" includes a single agent, as well as two or more agents; reference to "the invention" includes single and multiple aspects of an invention; and so forth.

The terms "agent", "compound", and "active" may be used interchangeably herein to refer to a substance that induces a desired pharmacological and/or physiological effect of antagonizing G-CSF, G-CSFR, G-CSF/G-CSFR interaction, G-CSF/G-CSFR-mediated signaling and/or expression of G-CSF or G-CSFR. The terms also encompass pharmaceutically acceptable and pharmacologically active forms thereof, including salts, Hence, the desired effect includes the inhibition of G-CSF activity or signaling or function and down regulation of expression of G-CSF or its receptor. By "down regulation of expression" includes "inhibition of expression" and means inhibiting or preventing or reducing transcription or translation or RNA processing leading to G-CSF or G-CSFR production. Hence, any form of reduction in G-CSF and/or G-CSFR levels is contemplated herein.

Agents contemplated herein which antagonize G-CSF or G-CSFR include:

a. an antibody specific for G-CSF or G-CSFR;
b. a soluble G-CSFR or a G-CSF-binding portion thereof;
c. a 20 to 30 nucleotide sense or antisense molecule targeted to a nucleic acid molecule encoding G-CSF the nucleic acid molecule comprising the sequence set forth in SEQ ID NO:3; or a 20 to 30 nucleotide sense or antisense molecule targeted to a nucleic acid molecule encoding a G-CSFR the nucleic acid molecule comprising the sequence set forth in SEQ ID NO:7.

Combination therapy involving the use of a G-CSF or G-CSFR antagonist together with another therapeutic agent such as an anti-inflammatory, immunosuppressive agent and/or other agent used in the treatment of an inflammatory neurodegenerative condition of the CNS is also contemplated by the present invention.

One particularly useful agent is an antibody specific or selective for a G-CSF or G-CSFR and/or which prevents G-CSF/G-CSFR interaction.

The terms "antibody" and "antibodies" include polyclonal and monoclonal antibodies and all the various forms derived from monoclonal antibodies, including but not limited to full-length antibodies (e.g. having an intact Fc region), antigen-binding fragments, including for example, Fv, Fab, Fab' and $F(ab')_2$ fragments; and antibody-derived polypeptides produced using recombinant methods such as single chain antibodies. The terms "antibody" and "antibodies" as used herein also refer to human antibodies produced for example in transgenic animals or through phage display, as well as chimeric antibodies, humanized antibodies, primatized antibodies or deimmunized antibodies. It also includes other forms of antibodies that may be therapeutically acceptable and antigen-binding fragments thereof, for example single domain antibodies derived from cartilage marine animals or Camelidae, or from libraries based on such antibodies. The selection of fragment or modified forms of the antibodies may also involve any effect the fragments or modified forms have on their half-lives. For example, it may in certain circumstances be advantageous for an antibody to have a short half-life to avoid global affects of anti-G-CSF/G-CSFR treatment, such as neutropenia. Alternatively, where exacerbations are common or likely, an antibody with a longer half-life may be advantageous. A "half-life" for an antibody is considered herein to be short if it is within 2 days or less. A longer half-life for an antibody would be any half-life in excess of 2 days and more particularly may be greater than 7 days.

The term "monoclonal antibody" is used herein to refer to an antibody obtained from a population of substantially homogeneous antibodies. That is, the individual antibodies comprising the population are identical except for naturally occurring mutations that may be present in minor amounts. The modifier "monoclonal" as used herein therefore indicates the character of the antibody as being obtained from a substantially homogeneous population of antibodies, and is not used to indicate that the antibody was produced by a particular method. For example, monoclonal antibodies in accordance with the present invention may be made by the hybridoma method described by Kohler and Milstein, Nature 256: 495-499, 1975, or may be made by recombinant DNA methods (such as described in U.S. Pat. No. 4,816,567). Monoclonal antibodies may also be isolated from phage antibody libraries using the techniques described in Clackson et al, Nature 352:624-628, 1991 or Marks et al, J. Mol. Biol. 222:581-597, 1991.

The terms "effective amount" and "therapeutically effective amount" as used herein mean a sufficient amount of an agent which provides the desired therapeutic or physiological effect or outcome, inhibiting G-CSF or G-CSFR or which inhibits expression of G-CSF or G-CSFR. In addition, the effect may be an amelioration of the symptoms of the inflammatory neurodegenerative condition of the CNS such as MS, Devic's disease or a viral infection in the brain. Undesirable effects, e.g. side effects, may sometimes manifest along with the desired therapeutic effect; hence, a practitioner balances the potential benefits against the potential risks in determining what is an appropriate "effective amount". The exact amount of agent required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using routine experimentation. For example, the ability of an anti-G-CSF/G-CSFR antibody to ameliorate the effects of MS, Devic's disease or a viral infection in the brain can be evaluated in an animal model system. One of ordinary skill in the art would be able to determine the required amounts based on such factors as the subject's size, the severity of the subject's symptoms, and the particular composition or route of administration selected.

Insofar as one embodiment of the present invention relates to the use of antibodies to G-CSF or its receptor, the effective amount include from about 10 µg/kg body weight to 20 mg/kg body weight of antibody such as 10, 20, 30, 40, 50, 60, 70, 80, 90, 100 µg/kg body weight, 100, 200, 300, 400, 500, 600, 700, 800, 900, 1000 µg/kg body weight or 2, 3, 4, 5, 6, 7, 8, 9, 10, 11, 12, 13, 14, 15, 16, 17, 18, 19 or 20 mg/kg body weight. Similar amounts are provided for single or combination therapy.

Reference to "an inflammatory neurodegenerative condition of the CNS" includes a disease condition of the CNS such as any exaggerated or excessive or prolonged inflammatory response in the CNS. Generally, the inflammatory neurodegenerative condition is associated with infiltration of neutrophils in the CNS. The CNS condition may be chronic or acute or a stage in between. Recurring acute forms such as exacerbations of a chronic condition are also contemplated by the present invention. The present invention is particularly directed to MS, Devic's disease (NMO) and a viral infection in the brain.

Generally, the agent is provided with a pharmaceutically or pharmacologically acceptable carrier, diluent or excipient.

A "pharmaceutically acceptable" carrier, diluent and/or excipient is a pharmaceutical vehicle comprised of a material that is not biologically or otherwise undesirable, i.e. the material may be administered to a subject along with the selected G-CSF/G-CSFR-antagonizing agent without causing any or a substantial adverse reaction. Carriers may include any and all solvents, dispersion media, coatings, antibacterial and antifungal agents, agents used for adjusting tonicity, buffers, chelating agents, and absorption delaying agents and the like.

Similarly, a "pharmacologically acceptable" salt of an agent as provided herein is a salt, that is not biologically or otherwise undesirable.

The terms "treating" and "treatment" as used herein refer to therapeutic treatment and may include prophylactic or preventative measures. For example, treatment may result in a reduction in severity and/or the frequency of symptoms of the inflammatory neurodegenerative condition of the CNS, the elimination of symptoms and/or underlying cause of the condition, the prevention of the occurrence of symptoms of the condition and/or their underlying cause and improvement or remediation or amelioration of damage following the inflammatory neurodegenerative condition. Such symptoms or characteristics include increased neutrophil infiltration, increased neutrophils in cerebral spinal fluid, increased release of neutrophil derived factors including but not limited to antimicrobial factors (such as myeloperoxidase and calprotectin), proteintases (such as elastase), acid hydrolases (such as cathepsins), chemokines and cytokines. Hence, the treatment may not result in a "cure" but rather an amelioration of symptoms. In addition, treatment may not commence until an exacerbating event occurs. In this context, the term "prophylactic" also applies to the prevention or treatment of a likelihood of an exacerbating event occurring. An example of an exacerbating event includes a stroke or other event of the systemic vasculature or an infection by a pathogenic agent such as a virus.

The antibodies may also be chimeric which include antibodies to G-CSF or G-CSFR comprising the heavy and light chain variable regions of rat or rabbit antibodies to G-CSF or G-CSFR and human heavy and light chain constant domains.

The terms "condition" and "disease" are used interchangeably throughout the subject specification.

A "subject" as used herein refers to an animal, particularly a mammal and more particularly a human who can benefit from the pharmaceutical compositions and methods of the present invention. There is no limitation on the type of animal that could benefit from the presently described pharmaceutical compositions and methods. A subject regardless of whether a human or non-human animal may be referred to as an individual, patient, animal, host or recipient as well as subject. The compounds and methods of the present invention have applications in human medicine and veterinary medicine.

Particular mammals are humans and laboratory test animals. Examples of laboratory test animals include mice, rats, rabbits, guinea pigs, hamsters, cats and dogs and primates.

One particularly useful agent of the present invention is an antibody to either G-CSF or G-CSFR that inhibits G-CSF signalling through the G-CSF receptor. Such antibodies to G-CSF may be referred to as anti-G-CSF antibodies, and antibodies to G-CSFR may be referred to as anti-G-CSFR antibodies. Where it is intended to refer to either an anti-G-CSF antibody or an anti-G-CSFR antibody it may simply refer to an anti-G-CSF/G-CSFR antibody or antibodies.

Although both polyclonal and monoclonal antibodies can be readily produced monoclonal antibodies are particularly preferred as they can be generated in large quantities, are highly specific and are directed against a single antigenic site. Furthermore, the monoclonal antibody preparations are homogeneous, making them ideal for generating antigen-binding fragments and other engineered antibody derivatives for therapeutic applications.

Although polyclonal antibodies are also relatively easily prepared, they are not as useful as monoclonal antibodies as polyclonal antibody preparations typically include different antibodies directed against different antigenic sites and thus are not as suitable for generating antigen-binding fragments and other engineered antibody derivatives for therapeutic applications.

The hybridoma method described above is used in animals, such as mice, to produce monoclonal antibodies. However, antibodies derived from animals are generally unsuitable for administration to humans as they may cause an immune response. As described below, such antibodies may be modified to become suitable for administration to humans or the desired non-human subject.

The anti-G-CSF/G-CSFR antibodies, for example, may also be produced using recombinant methods (for example, in an *E. coli* expression system) well known in the art. In this approach, DNA encoding monoclonal antibodies, such as the murine monoclonal antibodies of the present invention, may be isolated from the hybridoma cell lines, sequenced using standard procedures and optionally manipulated using recombinant DNA technology. For example, the DNA may be fused to another DNA of interest, or altered (such as by mutagenesis or other conventional techniques) to add, delete, or substitute one or more nucleic acid residues. The DNA may be placed into vectors which are then transfected or transformed into appropriate host cells using methods well known in the art (such as described in U.S. Pat. Nos. 4,399,216; 4,912,040; 4,740,461 and 4,959,455). The DNA isolated from the hybridoma cell lines may also be modified to change the character of the antibody produced by its expression.

For example, chimeric forms of murine anti-G-CSF/G-CSFR monoclonal antibodies may be produced by replacing the nucleotides encoding selected murine heavy and light chain constant domains with nucleotides encoding human heavy and light chain constant domains, such as is described in U.S. Pat. No. 4,816,567 and by Morrison et al, *Proc. Nat. Acad. Sci.* 81:6851, 1984. The chimeric antibodies may then be produced in an appropriate cell line, such as a murine myeloma cell line, that has been transfected with modified DNA.

Thus, among the antibodies contemplated by the present invention are chimeric anti-G-CSF/G-CSFR antibodies that comprise the heavy and light chain variable regions of a murine anti-G-CSF/G-CSFR monoclonal antibody fused to non-murine heavy and light chain antibody constant domains. In a particular embodiment, the non-murine heavy and light chain constant domains are human heavy and light chain antibody constant domains. Similarly, chimeric antibodies may include antibodies to G-CSF or G-CSFR comprising the heavy and light chain variable regions of rat or rabbit antibodies to G-CSF or G-CSFR and human heavy and light chain constant domains.

The anti-G-CSF/G-CSFR antibodies for use in the present invention also include humanized antibodies. In general, humanized antibodies are human antibodies (the recipient antibody) in which the complementarity determining (CDR) region residues have been replaced by CDR region residues from a non-human species (the donor antibody), such as from a mouse, rat, rabbit or non-human primate. In some cases, certain framework region (FR) residues of the human antibody may also be replaced by corresponding non-human residues, or the humanized antibodies may comprise residues which are not found in the recipient antibody or in the donor antibody. These modifications are made to enhance antibody performance and affinity. In general, the humanized antibody will comprise substantially all of at least one, and typically two, variable regions, in which all or substantially all of the CDR regions correspond to those of a non-human antibody, and all or substantially all of the FRs are those of a human antibody sequence. The humanized antibody may also optionally comprise at least a portion of an antibody constant region (Fc), typically that of a human antibody (Jones et al, *Nature* 321:522-525, 1986; Reichmann et al, *Nature* 332:323-329, 1988; Presta, *Curr. Op. Struct. Biol.* 2:593-596, 1992; Liu et al, *Proc. Natl. Acad. Sci. USA* 84:3439, 1987; Larrick et al, *Bio/Technology* 7:934, 1989; Winter & Harris, *TIPS* 14:139, 1993; Carter et al, *Proc. Nat. Acad. Sci.* 89:4285 1992). Similarly, to create a primatized antibody the murine CDR regions can be inserted into a primate framework using methods known in the art (see e.g. WO 93/02108 and WO 99/55369).

Alternatively, a humanized antibody may be created by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan et al, *Mol. Immunol.* 28:489-498, 1991 and Pedersen et al, *J. Mol. Biol.* 235:959-973, 1994). Therefore, it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region "invisible" to the human immune system. This procedure of humanization is referred to as "veneering" because only the surface of the antibody is altered, the supporting residues remain undisturbed.

Further, WO 2004/006955 describes methods for humanizing antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO 2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies.

The CDRs of a given antibody may be readily identified, for example using the system described by Kabat et al in *Sequences of Proteins of Immunological Interest,* 5th Ed., US Department of Health and Human Services, PHS, NIH, NIH Publication No. 91-3242, 1991).

In a particular embodiment, the antibodies for use in the present invention are human monoclonal antibodies. Such human monoclonal antibodies directed against G-CSF or G-CSFR can be generated using transgenic or transchromosomic mice carrying parts of the human immune system rather than the mouse system. These transgenic and transchromosomic mice include mice referred to herein as HuMAb mice and KM mice.

Still further, alternative transgenic animal systems expressing human immunoglobulin genes are available in the art and can be used to raise antibodies. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963.

Moreover, alternative transchromosomic animal systems expressing human immunoglobulin genes are available in the art and can be used to raise antibodies against G-CSF or G-CSFR. For example, mice carrying both a human heavy chain transchromosome and a human light chain transchromosome, referred to as "TC mice" can be used; such mice are described in Tomizuka et al, *Proc. Natl. Acad. Sci. USA* 97:722-727, 2000.

Human monoclonal antibodies can also be prepared using phage display methods for screening libraries of human immunoglobulin genes. Such phage display methods for isolating human antibodies are established in the art. See for example: U.S. Pat. Nos. 5,223,409; 5,403,484; and 5,571,698; U.S. Pat. Nos. 5,427,908 and 5,580,717; U.S. Pat. Nos. 5,969,108 and 6,172,197 and U.S. Pat. Nos. 5,885,793; 6,521,404; 6,544,731; 6,555,313; 6,582,915 and 6,593,081.

Human monoclonal antibodies can also be prepared using SCID mice into which human immune cells have been reconstituted such that a human antibody response can be generated upon immunization. Such mice are described in, for example, U.S. Pat. Nos. 5,476,996 and 5,698,767.

The anti-G-CSF/G-CSFR antibodies of the present invention also include antigen-binding fragments such as Fv, Fab, Fab' and F(ab')$_2$ fragments. Traditionally, antigen-binding fragments were generated by the proteolytic digestion of full antibodies (Morimoto et al, *Journal of Biochemical and Biophysical Methods* 24:107-117, 1992; Brennan et al, *Science* 229:81, 1985). A number of recombinant methods have now been developed for producing antigen-binding fragments of antibodies directly in recombinant host cells.

For example, Fab'-SH fragments can be directly recovered from *E. coli* and chemically coupled to form F(ab')$_2$ fragments (Carter et al, *Bio/Technology* 10:163-167, 1992). F(ab')$_2$ fragments can also be formed using the leucine zipper GCN4 to promote assembly of the F(ab')$_2$ molecule. Fv, Fab or F(ab')$_2$ fragments can also be isolated directly from recombinant host cell cultures. A number of recombinant methods have been developed for the production of single chain antibodies including those described in U.S. Pat. No. 4,946,778; Bird, *Science* 242:423, 1988, Huston et al, *Proc. Natl. Acad. Sci. USA* 85:5879, 1988 and Ward et al, *Nature* 334:544, 1989. Single chain antibodies may be formed by linking heavy ($V_H$) and light ($V_L$) chain variable region (Fv region) fragments via an short peptide linker to provide a single polypeptide chain (scFvs). The scFvs may also form dimers or trimers, depending on the length of a peptide linker between the two variable regions (Kortt et al, *Protein Engineering* 10:423, 1997). Phage display is another well known recombinant method for producing the antigen-binding fragments of the present invention.

The antigen-binding fragments of the present invention may be screened for desired properties. The assays described herein provide the means to identify antigen-binding fragments that bind to G-CSF or G-CSFR and which antagonize G-CSF signaling through G-CSFR.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g. Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9. cells, amphibian cells, bacterial cells, plant cells and fungal cells. When recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention from host cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

Antibodies expressed by different cell lines or in transgenic animals may have different glycosylation patterns from each other. However, all such antibodies to G-CSF or G-CSFR used in the treatment of immune-mediated inflammatory CNS conditions are part of the present invention, regardless of the glycosylation pattern of the antibodies.

Techniques are also known for deriving an antibody of a different subclass or isotype from an antibody of interest, i.e. subclass switching. Thus, IgG1 or IgG4 monoclonal antibodies may be derived from an IgM monoclonal antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g. DNA encoding the constant region of an antibody of the desired isotype.

Vectors available for cloning and expression in host cell lines are well known in the art, and include but are not limited to vectors for cloning and expression in mammalian cell lines, vectors for cloning and expression in bacterial cell lines, vectors for cloning and expression in phage and vectors for cloning and expression insect cell lines. The antibodies can be recovered using standard protein purification methods.

In a particular embodiment, antibodies for use in the method of the present invention are human or humanized anti-G-CSF/G-CSFR antibodies which antagonize G-CSF signaling via G-CSFR.

Particularly, the human or humanized anti-G-CSF/G-CSFR antibodies are in isolated, homogenous or fully or partially purified form.

More particularly, the human or humanized anti-G-CSF/G-CSFR antibodies are full-length monoclonal antibodies or antigen-binding fragments.

As indicated above, the selection of antigen-binding fragments or modified forms of the antibodies may be influenced by the effect the fragments or modified forms have on the individual half-life.

Another example of a useful agent is a soluble form of the G-CSFR which competes with the naturally occurring membrane-associated G-CSFR for G-CSF interaction. Those skilled in the art can readily prepare soluble forms of the receptor, see for example U.S. Pat. No. 5,589,456 and Honjo et al, *Acta Crystallograph Sect F Struct Biol Cryst Commun.* 61 (Pt 8):788-790, 2005.

Alternatively, agents can be screened for their ability to bind to G-CSF or G-CSFR-genetic materials. In one embodiment, G-CSF- or G-CSFR-encoding cDNA or genomic DNA or mRNA transcript or portion thereof such as an EST or SAGE tag is immobilized to a solid support such as a nanoparticle or microsphere. Potential agents are then brought into contact with the immobilized nucleic acid molecules and binding detected by change in radiation, emissions, atom excitation, mass and/or density.

Once identified, the agent is eluted off the nucleic acid molecule and characterized in more detail. For example, agents which bind to G-CSF/G-CSFR genetic material may inhibit expression (transcription and/or translation).

The present invention further contemplates using chemical analogs of G-CSF or G-CSFR as antagonists of G-CSF or its receptor. As indicated above, soluble G-CSF receptors may also be employed.

Chemical analogs contemplated herein include, but are not limited to, modifications of side chains, incorporation of unnatural amino acids and/or their derivatives during peptide, polypeptide or protein synthesis and the use of crosslinkers and other methods which impose conformational constraints on the proteinaceous molecule or their analogs.

Other agents contemplated by the present invention include nucleic acid molecules such as RNA or DNA which are useful for inducing silencing by antisense- or sense-mediated mechanisms of genes encoding the cytokines or their receptors. Sense-mediated gene silencing is also referred to as co-suppression and involves a range of mechanisms including the induction of RNAi. Transcriptional and post transcriptional gene silencing is therefore, contemplated by the present invention.

The terms "nucleic acids", "nucleotide" and "polynucleotide" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog (such as the morpholine ring), internucleotide modifications such as uncharged linkages (e.g. methyl phosphonates, phosphotriesters, phosphoamidates, carbamates, etc.), charged linkages (e.g. phosphorothioates, phosphorodithioates, etc.), pendent moieties (e.g. polypeptides), intercalators (e.g. acridine, psoralen, etc.), chelators, alkylators and modified linkages (e.g. α-anomeric nucleic acids, etc.). Also included are synthetic molecules that mimic polynucleotides in their ability to bind to a designated sequence via hydrogen binding and other chemical interactions. Such molecules are known in the art and include, for example, those in which peptide linkages substitute for phosphate linkages in the backbone of the molecule.

Antisense polynucleotide sequences, for example, are useful in silencing transcripts of the G-CSF genetic sequence or the G-CSFR genetic sequence (see Geng et al, *Molecular Immunology* 44:5121-529, 2007). Furthermore, polynucleotide vectors containing all or a portion of the G-CSF gene locus may be placed under the control of a promoter in either the sense or antisense orientation and introduced into a cell. Expression of such a sense or antisense construct within a cell interferes with target transcription and/or translation. Furthermore, co-suppression (i.e. using sense-suppression) and mechanisms to induce RNAi or siRNA may also be employed. Alternatively, antisense or sense molecules may be directly administered. In this latter embodiment, the antisense or sense molecules may be formulated in a composition and then administered by any number of means to target cells.

A variation on antisense and sense molecules involves the use of morpholinos, which are oligonucleotides composed of morpholine nucleotide derivatives and phosphorodiamidate linkages (for example, Summerton and Weller, *Antisense and Nucleic Acid Drug Development* 7:187-195, 1997).

In one embodiment, the present invention employs compounds such as oligonucleotides and similar species for use in modulating the function or effect of nucleic acid molecules encoding G-CSF or G-CSFR, i.e. the oligonucleotides induce transcriptional or post-transcriptional gene silencing. This is accomplished by providing oligonucleotides which specifically hybridize with one or more nucleic acid molecules encoding the target nucleic acid. The oligonucleotides may be provided directly to a cell or generated within the cell. As used herein, the terms "target nucleic acid" and "nucleic acid molecule encoding G-CSF or G-CSFR" have been used for convenience to encompass the encoding DNA, RNA (including pre-mRNA and mRNA or portions thereof) transcribed from such DNA, and also cDNA derived from such RNA. The hybridization of a compound of the subject invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired.

"Complementary" as used herein, refers to the capacity for precise pairing between two nucleobases of an oligomeric compound. For example, if a nucleobases at a certain position of an oligonucleotide (an oligomeric compound), is capable of hydrogen bonding with a nucleobases at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid. One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products.

In the context of the subject invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those herein described.

For topical delivery of antisense compounds, these oligonucleotides may contain modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Particular modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Sense and antisense nucleotides sequences contemplated herein particularly include 20 to 30 nucleotide bases in length. Reference to "20 to 30" includes 20, 21, 22, 23, 24, 25, 26, 27, 28, 29 or 30 or their equivalents outside the range 20 to 30 nucleotides. The terms "nucleobases" and "nucleotides" may be used interchangeably. Particularly useful sense and antisense molecules are directed to the G-CSF gene or mRNA (SEQ ID NOs:2 and 3) encoding the mature protein (SEQ ID NO:4) or to the G-CSFR gene or mRNA (SEQ ID NOs:6 and 7) encoding the mature protein (SEQ ID NO:8).

Whilst sense or antisense molecules directed to the G-CSF gene or mRNA or G-CSFR gene or mRNA sense or antisense molecules are contemplated against any portion of the coding or non-coding regions including leader sequence and selected introns or extons of the G-CSF or G-CSFR gene or mRNA. Hence, sense and antisense molecules of 20 to 30 nucleotide basis in length are contemplated to one or more of SEQ ID NOs:2, 3, 6 or 7.

In an alternative embodiment, genetic constructs including DNA "vaccines" are used to generate antisense or sense molecules mammalian cells. Furthermore, many of the preferred features described above are appropriate for sense nucleic acid molecules.

This aspect of the present invention can be worked implemented by conventional molecular biology and recombinant DNA techniques. The techniques are well known in the art and are described in various publications, such as Sambrook, Fritsch & Maniatis, *Molecular Cloning: A Laboratory Manual*, Second Edition (1989) Cold Spring Harbor Laboratory Press, Cold Spring Harbor, N.Y.; DNA Cloning: *A Practical Approach*, Volumes I and II, D. N. Glover ed. 1985 and Ausubel et al. (eds.), *Current Protocols in Molecular Biology*, John Wiley & Sons, Inc., 1994.

Nucleic acids of the present invention may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

A "promoter" or "promoter sequence" is a DNA regulatory region capable of binding an RNA polymerase in a cell and initiating transcription of a coding sequence. A promoter sequence is generally bounded at its 3' terminus by the transcription initiation site and extends upstream in the 5' direction to include the minimum number of bases or elements necessary to initiate transcription at any level. A transcription initiation site as well as protein binding domains (consensus sequences) responsible for the binding of RNA polymerase may be found within the promoter sequence. The promoter may be operably associated with other expression control sequences, including enhancer and repressor sequences or with a nucleic acid of the invention. Promoters which may be used to control gene expression include, but are not limited to, cytomegalovirus (CMV) promoter and the SV40 early promoter region.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be trans-RNA spliced (if it contains introns) and, optionally, translated into a protein encoded by the coding sequence.

The terms "express" and "expression" mean allowing or causing the information in a gene, RNA or DNA sequence to be converted into a product; for example, producing a protein by activating the cellular functions involved in transcription and translation of a nucleotide sequence. A DNA sequence is expressed in or by a cell to form an "expression product" such as RNA (such as mRNA or a double stranded short RNA, hairpin RNA or antisense RNA) or a protein (such as an antagonist of cytokine activity or portion of an anti-cytokine antibody). The expression product itself may also be said to be "expressed" by the cell.

The terms "vector", "cloning vector" and "expression vector" mean the vehicle (such as a plasmid) by which a DNA or RNA sequence can be introduced into a host cell, so as to transform the host and, optionally, promote expression and/or replication of the introduced sequence.

The term "transfection" or "transformation" means the introduction of a nucleic acid into a cell. These terms may refer to the introduction of a nucleic acid encoding a cytokine cross-reactive antibody or a fragment thereof into a cell. A host cell that receives the introduced DNA or RNA has been "transformed" and is a "transformant" or a "clone". The DNA or RNA introduced to a host cell can come from any source, including cells of the same genus or species as the host cell, or cells of a different genus or species.

The term "host cell" means any cell of any organism that is selected, modified, transfected, transformed, grown, or used or manipulated in any way, for the production of a substance by the cell, for example the expression of a protein or the replication of a gene.

The term "expression system" means a host cell and compatible vector which, under suitable conditions, can express a protein or nucleic acid which is carried by the vector and introduced to the host cell. Common expression systems include *E. coli* host cells and plasmid vectors, insect host cells and Baculovirus vectors, and mammalian host cells and vectors.

Agents (e.g. antibodies, proteins such as non-signalling mutant forms of G-CSF, small chemical molecules, soluble receptors, etc) identified in accordance with the present invention are conveniently supplied in pharmaceutical compositions.

Composition forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include agents to adjust tonicity, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

When the modulator is suitably protected, it may be orally administered, for example, with an inert diluent or with an assimilable edible carrier, or it may be enclosed in hard or soft shell gelatin capsule, or it may be compressed into tablets, or it may be incorporated directly with the food of the diet or administered via breast milk. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of modulator. The percentage of the compositions and preparations may, of course, be varied and may conveniently be between about 5 to about 80% of the weight of the unit. The amount of modulator in such therapeutically useful compositions is such that a suitable dosage will be obtained. Preferred compositions or preparations according to the present invention are prepared so that an oral dosage unit form contains between about 0.1 µg and 200 mg of modulator. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules, creams and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and anti-fungal agents, isotonic and absorption delaying agents and the like. The use of such media and agents for pharmaceutical active agents is well known in the art and except insofar as any conventional media or agent is incompatible with the modulator, their use in the therapeutic compositions is contemplated. Supplementary active compounds can also be incorporated into the compositions.

As indicated above, administration may be by any means.

Dosage regimens may be adjusted to provide the optimum desired response (e.g. a therapeutic response). For example, a single bolus may be administered, several divided doses may be administered over time or the dose may be proportionally reduced or increased as indicated by exigencies of the therapeutic situation. It is especially advantageous to formulate parenteral compositions in dosage unit form for ease of administration and uniformity of dosage.

A physician or veterinarian having ordinary skill in the art can readily determine and prescribe the effective amount of the pharmaceutical composition required. For example, the physician or veterinarian could start doses of the anti-G-CSF/G-CSFR antibody of the present invention, employed in the pharmaceutical composition at levels lower than that required in order to achieve the desired therapeutic effect and gradually increase the dosage until the desired effect is achieved. In general, a suitable daily dose of a composition of the invention may be that amount of the compound which is the lowest dose effective to produce a therapeutic effect. Such an effective dose will generally depend upon the factors described above. It is preferred that administration be by injection, preferably proximal to the site of the target (e.g. lung). If desired, the effective daily dose of a pharmaceutical composition may be administered as two, three, four, five, six or more subdoses administered separately at appropriate intervals throughout the day.

For therapeutic applications, the anti-G-CSF/G-CSFR antibodies are administered to a mammal, preferably a human, in a pharmaceutically acceptable dosage form such as those discussed above, including those that may be administered to a human intravenously as a bolus or by continuous infusion over a period of time.

The composition may also comprise genetic molecules such as a vector capable of transfecting target cells where the vector carries a nucleic acid molecule capable of encoding a modulator, when the modulator is a proteinaceous molecule. The vector may, for example, be a viral vector. In this regard, a range of gene therapies are contemplated by the present invention including isolating certain cells, genetically manipulating and returning the cell to the same subject or to a genetically related or similar subject.

Hence, the present invention contemplates a further aspect of the present invention contemplates a method for the treatment of an inflammatory neurodegenerative condition of the CNS in a subject, the method comprising administering to the subject an amount of an agent effective to inhibit G-CSF or G-CSFR or inhibit expression G-CSF or G-CSFR.

Another aspect provides a method for treating an inflammatory neurodegenerative condition of the CNS, the method comprising administering to the subject a G-CSF or G-CSFR inhibiting agent selected from the group consisting of:

a. an antibody specific for G-CSF or G-CSFR;
    b. a soluble G-CSFR or a G-CSF-binding portion thereof;
    c. a 20 to 30 nucleotide sense or antisense molecule targeted to a nucleic acid molecule encoding G-CSF, the nucleic acid molecule comprising the sequence set forth in SEQ ID NO:3; or a 20 to 30 nucleotide sense or antisense molecule targeted to a nucleic acid molecule encoding a G-CSFR, the nucleic acid molecule comprising the sequence set forth in SEQ ID NO:7.

In another aspect, the present invention is directed to a method for the treatment of MS or Devic's disease in a subject, the method comprising administering to the subject an amount of an agent effective to inhibit the activity of G-CSF or G-CSFR or inhibit expression of G-CSF or G-CSFR.

Another aspect of the present invention relates to a method for the treatment of an inflammatory neurodegenerative condition of the CNS such as but not limited to MS, Devic's disease and a viral infection in the brain in a subject, the method comprising administering an agent which inhibits G-CSF or G-CSFR or inhibits the expression of G-CSF or G-CSFR and at least one other therapeutic agent such as an anti-inflammatory agent, immunosuppressive agent or other agent used in the treatment of an inflammatory neurodegenerative condition of the CNS.

In a particular embodiment, the present invention contemplates a method for the treatment of MS, Devic's disease or a viral infection in the brain in a subject the method comprising administering to the subject an amount of an antibody or antigen-binding portion thereof effective to inhibit the activity of G-CSF or G-CSFR or G-CSF/G-CSFR interaction.

The present invention further contemplates the use of an agent which inhibits the activity of G-CSF or G-CSFR, or which inhibits the expression of G-CSF or G-CSFR in the manufacture of a medicament in the treatment of an inflammatory neurodegenerative condition to CNS in a subject.

Still a further aspect contemplates the use of an agent which inhibits G-CSF or G-CSFR or which inhibits expression of G-CSF or G-CSFR in the manufacture of a medicament for treating an inflammatory neurodegenerative condition of the CNS wherein the agent is selected from the group consisting of:

a. an antibody specific for G-CSF or G-CSFR;
b. a soluble G-CSFR or a G-CSF-binding portion thereof;
c. a 20 to 30 nucleotide sense or antisense molecule targeted to a nucleic acid molecule encoding G-CSF, the nucleic acid molecule comprising the sequence set forth in SEQ ID NO:3; or a 20 to 30 nucleotide sense or antisense molecule targeted to a nucleic acid molecule encoding a G-CSFR, the nucleic acid molecule comprising the sequence set forth in SEQ ID NO:7.

In a particular embodiment, the present invention is directed to the use of an antibody to G-CSF or G-CSFR in the manufacture of a medicament for the treatment of MS, Devic's disease or a viral infection in the brain in a subject.

In accordance with these aspects of the present invention, the inflammatory neurodegenerative condition of the CNS is one associated or characterized by infiltration of neutrophils. Particular conditions are MS, Devic's disease and a viral infection in the brain.

Animal models useful for testing inhibition of G-CSF or its receptor, or other approaches to antagonism of G-CSF-mediated signaling, include the experimental autoimmune encephalomyelitis (EAE) model.

In accordance with the present invention, suppression of G-CSF with a test antagonist had a significant impact on neutrophil number in the EAE model and reduced the level of disease in the model. As neutrophils are key mediators of CNS inflammation, the significant reduction in neutrophil numbers induced by the G-CSF antagonist in the EAE model indicates that the antagonism of G-CSF activity is a useful therapeutic approach.

The present invention is further described by the following non-limiting Examples. In the Examples the following materials and methods are employed.

Animals

Female C57Bl/6 mice or G-CSF KO mice (provided by A. Dunn, Ludwig Institute for Cancer Research, Parkville, Australia) were used.

Drug Administration

Mice were given the specified doses of isotype control or anti-GSCF antibody (as outlined in section 1) once daily, administered by i.v. injection.

Antibodies

For analysis of neutrophil number anti-CD11b (M1/70) and anti-GR1 (1A8) were purchased from BD pharmingen (San Diego, Calif., USA). Isotype control (rat IgG1) HRPN was purchased from BioXcell (West Lebanon, N.H., USA). Neutralizing anti-G-CSF (MAB414) was purchased from R&D systems (Minneapolis, Minn., USA).

Experimental Autoimmune Encephalomyelitis (EAE)

EAE was induced in female mice aged 8-12 weeks. Mice were immunized subcutaneously with 100 μg of myelin peptide$_{35-55}$ MOG (Mimotopes, Clayton, Vic, Australia) emulsified in CFA (Difco, BD San Diego, Calif., USA), followed by 200 ng pertussis toxin (Sigma-Aldrich, St Louis, Mo., USA) administered intravenously on d0 and d2. Clinical paralysis score was assessed as described previously (Langrish et al, *J Exp Med* 201 (2):233-40, 2005) with a maximum score of 6 for each mouse.

Assessment of Neutrophil Numbers

For analysis of neutrophil numbers during anti-G-CSF treatment in EAE, animals were sacrificed at d0 (no treatment), d7, d14 and d21. Single cell suspensions were made from spleen and cervical LN and red blood cells removed by hypotonic lysis with Red cell lysis buffer (Sigma-Aldrich, St Louis, Mo., USA). For blood analysis, red cells were removed by hypotonic lysis. For bone marrow analysis, femurs were removed and flushed with ice cold PBS and red cells were removed by hypotonic lysis. For analysis of CNS cells, mononuclear cells were isolated as previously described (Langrish et al, 2005 supra). Single cell suspensions of spleen, blood, lymph node, bone marrow and CNS cells were stained with anti-CD11b and GR1 antibodies (1/100 dilution), washed and run on FACS Canto (BD, San Jose, Calif., USA). Data was analyzed using Flowjo software (Treestar, Ashland Oreg., USA).

T Cell Reactivation and Cytokine Assays

Spleen, Inguinal, auxiliary and brachial LN were harvested from mice 10 days post subcutaneous immunization with MOG/CFA. Cells were isolated by homogenization through a 70 μm filter, then washed twice in medium and pooled for each treatment group. CD4+ T-cells were then purified by MACS positive selection according to the manufactures instructions (Miltenyi Biotec, Bergisch Gladbach, Germany). T-cell purity was >95% CD4+ as determined by FACS. $2 \times 10^5$ purified CD4+ T cells were cultured with $2 \times 10^5$ irradiated splenocytes in 0.2 ml in triplicate wells in 96 well plates with 100 μg/ml of MOG$_{35-55}$ peptide for 3 days. Supernatant was harvested and cytokines measured by Milliplex assay (Millipore, Billerica, Mass., USA) on a Luminex 200 instrument (Austin, Tex., USA) according the manufactures instructions.

Statistical Analysis

Two tailed Mann-Whitney test used to generate statistical analysis were performed using the Prism [Trade Mark] software.

EXAMPLE 1

G-CSF Deficient Mice are Protected from Clinical Signs of Disease in EAE Model of Neurological Autoimmune Inflammation To test the role of G-CSF in neurological autoimmune inflammation the Experimental Autoimmune Encephalomyelitis (EAE) mouse model was used. EAE is a widely used animal model that replicates many of the clinical and histopathological signs of MS and Devic's disease including degeneration of motor neuron function.

EAE was induced in wild type (C57Bl/6) or G-CSF knock out (KO) mice. Disease was monitored from day 0 to 30 and clinical paralysis scored.

It was found that mice deficient in G-CSF (G-CSF Knock-out mice, G-CSF KO) were protected from progressive motor neuron dysfunction (FIG. 1). This indicated that in vivo, G-CSF plays an important pro-inflammatory role in the pathogenic mechanisms of autoimmune CNS destruction.

EXAMPLE 2

Figure 2:
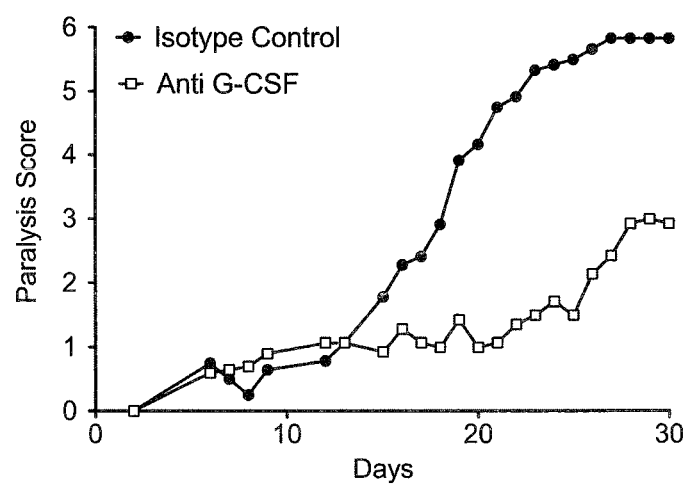
FIG. 2 is a graphical representation showing that blocking the action of G-CSF with an anti-G-CSF antibody inhibits disease progression in the EAE model in wild type (C57Bl/6) mice compared with isotype control treated animals. Disease was monitored from day 0 to 30 and paralysis scores determined as noted in the experimental section.

Blocking G-CSF Inhibits Clinical Signs of Disease in EAE Model of Neurological Autoimmune Inflammation To test whether therapeutic inhibition of G-CSF was beneficial in vivo, EAE was induced in wild-type mice as described above and treated them with a neutralizing anti-G-CSF monoclonal antibody (mAb). It was found that treatment of mice with a neutralizing anti-G-CSF mAb inhibited the clinical progression of EAE (FIG. 2). Anti-G-CSF did not effect the mean day of clinical onset (score 1) [Table 3] or the mean day to peak disease (Table 4). However, treatment with a neutralizing anti-G-CSF mAb inhibited the average clinical score and protected animals from progressive paralysis (Table 5). Therefore, disease progression after initial onset is slowed.

TABLE 3

Mean day of disease onset

| Treatment | Mean day of onset (+/−std er) |
|---|---|
| Isotype Control | 7.25 (+/−0.8) |
| Anti-G-CSF | 8.8 (+/−1.2) |

*not significant

TABLE 4

Mean day to peak clinical score

| Treatment | Mean day to peak disease score (+/−std er) |
|---|---|
| Isotype Control | 20.4 (+/−1.4) |
| Anti-G-CSF | 22.3 (+/−2.1) |

*not significant

TABLE 5

Mean clinical score

| Treatment | Mean peak clinical score (+/−std er) |
|---|---|
| Isotype Control | 5.7 (+/−0.18) |
| Anti-G-CSF | 3.0 (+/−0.7) |

*p = 0.005.

EXAMPLE 3

Anti-G-CSF Treatment Inhibits Disease Induced Neutrophila in EAE Model of Neurological Autoimmune Inflammation To assess the effect of G-CSF blockade on neutrophil numbers in vivo, a time course analysis was performed during isotype control or anti-G-CSF treatment in the EAE model described above. Animals were sacrificed at d0 (no treatment), d7, d14 and d21 and neutrophil numbers assessed.

Figure 3:
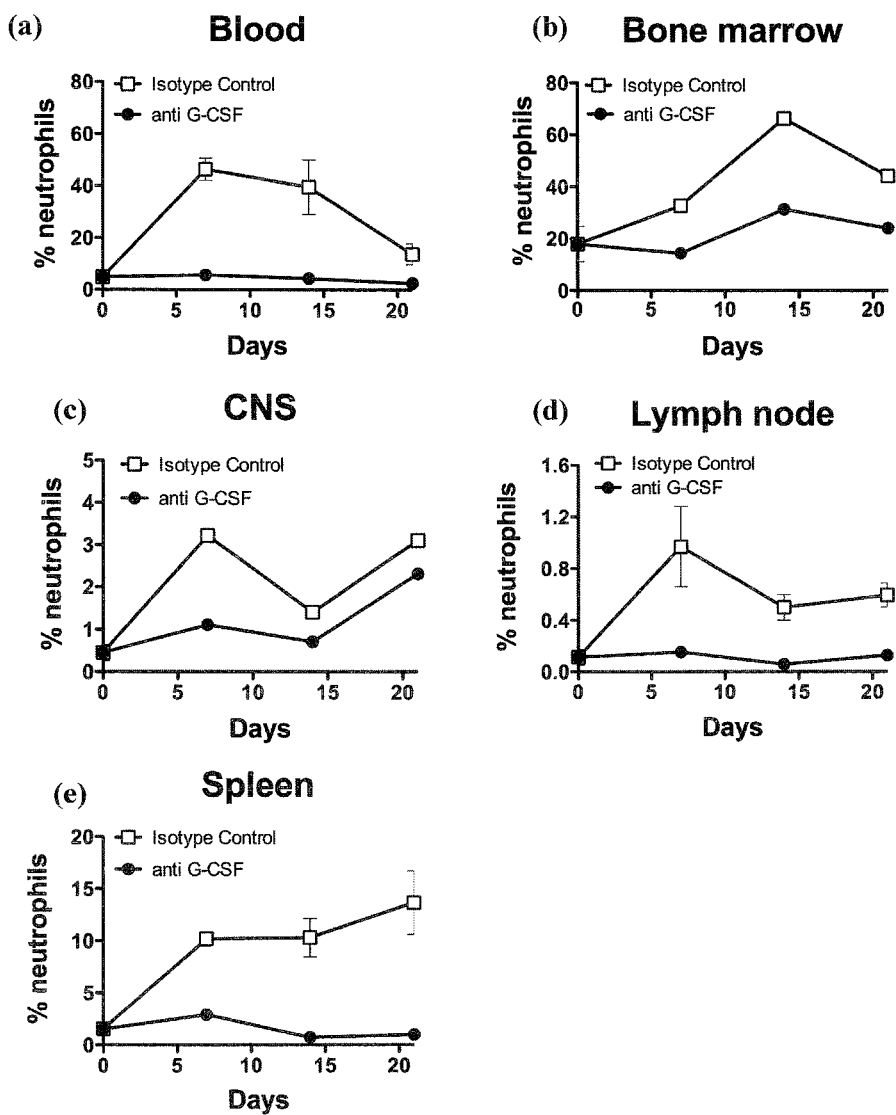
FIGS. 3a through e are graphical representations of a time course analysis of the percentage of neutrophils in various samples taken from isotype control and anti-G-CSF antibody treated animals.

After induction of EAE, neutrophil numbers increased in the blood, bone marrow, CNS, lymph node and spleen (FIG. 3). Treatment with anti-G-CSF inhibited neutrophilia at all of these sites (FIG. 3), consistent with a key role for G-CSF in controlling neutrophil responses in vivo.

EXAMPLE 4

Anti-G-CSF Treatment Inhibits Proinflammatory T Cell Cytokines in EAE Model of Neurological Autoimmune Inflammation CD4+ T cell cytokines are important regulators of inflammation. To elucidate the effect of anti-G-CSF treatment on this pathway purified CD4+ T cells were used from the spleens and lymph nodes of day 10 sacrificed animals from both isotype control or anti-G-CSF treated mice in the EAE model described above, and reactivated the purified CD4+ T cells in-vitro with MOG and analyzed cytokine expression.

Figure 4:
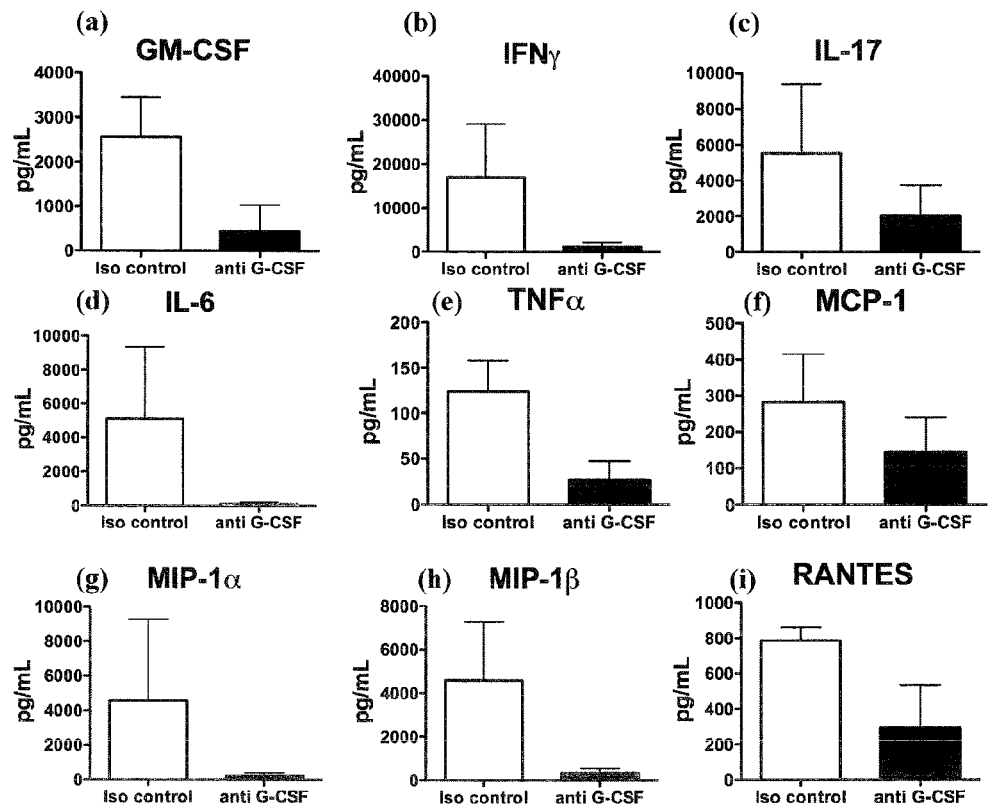
FIGS. 4a through i are representations showing the levels of various cytokines following reactivation of T cells purified from both isotype control and anti-G-CSF antibody treated animals sacrificed at Day 10.

Anti-G-CSF treatment inhibited the expression of proinflammatory cytokines in response to reactivation. Anti-G-CSF treatment reduced the expression of IL-6, TNFα, GM-CSF and IL-17, all important cytokines for driving EAE (FIG. 4). Anti-G-CSF treatment also inhibited the expression of CC-family chemokines important for cell recruitment during neurological inflammation (Boven et al, *Clin Exp Immunol* 122 (2):257-63, 2000). Expression of MIP-1α, MIP-1β, MCP-1 and RANTES by CD4+ T cell during reactivation was inhibited by anti-G-CSF treatment in vivo (FIG. 4).

EXAMPLE 5

Inhibition of G-CSF Mediated Proliferation in hG-CSF Receptor Expressing Ba/F3 Cells by Various G-CSF Antagonists BaF3 cells stably transfected with hG-CSFR as described by Layton et al, *J. Biol. Chem.* 272:29735-29741, 1997 were cultured in 96 well plates at 20,000 cells/well in DMEM media with 5% v/v FBS and 0.5 ng/ml rh or mGCSF (R&D Systems Cat #214-CS and Cat#414-CS respectively). G-CSF antagonists (R&D Systems MAB414, anti-hG-CSFR mAb711 and hG-CSFR-Fc) were added at threefold titrating doses starting from 1 μM and cell proliferation measured by MTS reduction (Cory et al, *Cancer Commun.* 3:207-12, 1991; Riss and Moravec, *Mol. Cell. Biol.* 3 (1):184a, 1993) after 48 hours culture.

A. Inhibition by Anti-G-CSF Antibody:
Anti-G-CSF was able to inhibit mG-CSF proliferation with an $IC_{50}$ of 10 pM.

B. Inhibition by Anti-hG-CSFR Antibody:
A murine monoclonal antibody against the hG-CSF Receptor, mAb711, (Layton et al, supra 1997) and its humanized derivative were able to inhibit mG-CSF proliferation with $IC_{50}$'s of 1.1 nM and 1.5 nM respectively.
A chimeric antibody comprising the heavy and light chain variable regions of mAb711 and human IgG1 heavy and light chain constant regions inhibited G-CSF activity with a similar $IC_{50}$ to the murine monoclonal antibody mAb711.

C. Inhibition by Soluble hG-CSFR-Fc Protein:
A soluble G-CSFR-Fc protein (Honjo et al, *Acta Cryst F*61: 788-790, 2005) was able to inhibit mG-CSF proliferation with an $IC_{50}$ of 22 pM.

These results demonstrate that the biological activity of G-CSF is inhibited by a variety of antagonists, including but not limited to, antibodies to G-CSF, antibodies to G-CSFR, and soluble G-CSF receptors.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Alonso et al, *Neurology* 71 (2): 129-35, 2008
Barahona-Gamido et al, *Biologics* 2 (3):501-4, 2008
Bergamaschi et al, *Neuroepidemiology* 25 (1): 15-8, 2005
Bialek et al, *Infection* 26 (6):375-8, 1998
Bird, *Science* 242:423, 1988
Boven et al, *Clin Exp Immunol* 122 (2):257-63, 2000
Brennan et al, *Science* 229:81, 1985
Bungart et al, *British Journal of Haematology* 22:1156, 1990
Carter et al, *Bio/Technology* 10:163-167, 1992
Clackson et al, *Nature* 352:624-628, 1991
Colotta et al, *Blood* 80:2012-2020, 1992
Cory et al, *Cancer Commun.* 3:207-12, 1991
Dagia et al, *Nat Med* 12 (10):1185-90, 2006
de Haan et al, *Blood* 86:2986-2992, 1995
Demetri et al, *Blood* 78:2791-2808, 1991
Dibbert et al, *Proc Natl Acad Sci USA* 96 (23):13330-5, 1999
Eyles et al, *Blood* 112 (13):5193-201, 2008
Frank et al, *BMC Neurosci* 10:49, 2009
Geng et al, *Molecular Immunology* 44:5121-529, 2007
Gericke et al, *Journal of Leukocyte Biology* 57:455-461, 1995
Hadaya et al, *J Autoimmun* 24 (2):125-34, 2005
Honjo et al, *Acta Crystallograph Sect F Struct Biol Cryst Commun.* 61 (Pt 8):788-790, 2005
Huston et al, *Proc. Natl. Acad. Sci. USA* 85:5879, 1988
Jacob et al, *Blood* 92:353-361, 1998
Jones et al, *Nature* 321:522-525, 1986
Kabat et al in *Sequences of Proteins of Immunological Interest,* 5th Ed., US Department of Health and Human Services, PHS, NIH, NIH Publication No. 91-3242, 1991
Kohler and Milstein, *Nature* 256:495-499, 1975
Kortt et al, *Protein Engineering* 10:423, 1997
Kudo et al, *Scand J Gastroenterol* 43 (6):689-97, 2008
Langrish et al, *J Exp Med* 201 (2):233-40, 2005
Larrick et al, *Bio/Technology* 7:934, 1989
Layton et al, *J. Biol. Chem.* 272:29735-29741, 1997
Liu et al, *Proc. Natl. Acad. Sci. USA* 84:3439, 1987
Lopez-Diego et al, *Nat Rev Drug Discov* 7 (11): 909-25, 2008
Lord et al, *Proc. Natl. Acad. Sci. USA* 86:9499-9503, 1989
McColl et al, *J Immunol* 161 (11):6421-6, 1998
Marks et al, *J. Mol. Biol.* 222:581-597, 1991
Metcalf, *International Journal of Cancer* 25:225, 1980
Morales et al, *Adv Neurol* 98:27-45, 2006
Morimoto et al, *Journal of Biochemical and Biophysical Methods* 24:107-117, 1992
Morrison et al, *Proc. Nat. Acad. Sci.* 81:6851, 1984
Nicola et al, *Journal of Biological Chemistry* 258:9017, 1983
Nicola et al, *Nature* 314:625, 1985
Openshaw et al, "*Neurology* 54 (11):2147-50, 2000
Padlan et al, *Mol. Immunol.* 28:489-498, 1991
Pedersen et al, *J. Mol. Biol.* 235:959-973, 1994
Presta, *Curr. Op. Struct. Biol.* 2:593-596, 1992
Ragonese et al, *Eur J Neurol* 15 (2):123-7, 2008
Reichmann et al, *Nature* 332:323-329, 1988
Rex et al, *Transfusion* 35:605-611, 1995
Riss and Moravec, *Mol. Cell. Biol.* 3 (1):184a, 1993
Roberts et al, *Blood* 89:2736-2744, 1997
Rutella et al, *Transplantation* 84 (1 Suppl):S26-30, 2007
Sambrook, Fritsch & Maniatis, *Molecular Cloning: A Laboratory Manual*, Second Edition (1989) Cold Spring Harbor Laboratory Press, Cold Spring Harbor, N.Y.; DNA Cloning: *A Practical Approach*, Volumes I and II, D. N. Glover ed. 1985 and Ausubel et al. (eds.), *Current Protocols in Molecular Biology*, John Wiley & Sons, Inc., 1994
Snir et al, *J Neuroimmunol* 172 (1-2):145-55, 2006
Souza et al, *Science* 232:61, 1986
Summerton and Weller, *Antisense and Nucleic Acid Drug Development* 7:187-195, 1997
Ward et al, *Nature* 334:544, 1989
Weiner et al, *J Neurol* 255 (Suppl 1): 3-11, 2008
Welte et al, *Blood* 88:1907-1929, 1996
Wingerchuk et al, *Lancet Neurol* 6 (9):805-15, 2007
Wingerchuk et al, *Curr Treat Options Neurol* 10 (1):55-66, 2008
Winter & Harris, *TIPS* 14:139, 1993; Carter et al, *Proc. Nat. Acad. Sci.* 89:4285 1992
Xu et al, *British Journal of Haematology* 93:558-568, 1996
Yong et al, *European Journal of Haematology* 49:251-259, 1992
Yong, *British Journal of Haematology* 94:40-47, 1996
Zavala et al, *J Immunol* 168 (4):2011-9, 2002
Zehntner et al, *J Immunol* 174 (8):5124-31, 2005

The invention claimed is:

1. A method for treating an inflammatory neurodegenerative condition of the CNS in a subject wherein the inflammatory neurodegenerative condition is Multiple Sclerosois (MS), said method comprising administering to said subject an antibody specific for G-CSFR.

2. The method of claim 1, wherein the G-CSFR antibody is an antigen binding fragment specific for G-CSFR.

3. The method of claim 1 wherein the subject is a human.

4. The method of claim 1 further comprising the administration of a therapeutic agent selected from the group consisting of an anti-inflammatory agent, immunosuppressive agent or other agent used in the treatment of an inflammatory neurodegenerative condition of the CNS.

5. The method of claim 1 wherein the antibody specific for G-CSFR is a monoclonal antibody.

6. The method of claim 1 wherein the antibody is a chimeric, human or humanized antibody.

7. The method of claim 1 wherein the antibody is a human antibody.

* * * * *